US009558570B2

(12) United States Patent
Liang et al.

(10) Patent No.: US 9,558,570 B2
(45) Date of Patent: Jan. 31, 2017

(54) ITERATIVE RECONSTRUCTION FOR X-RAY COMPUTED TOMOGRAPHY USING PRIOR-IMAGE INDUCED NONLOCAL REGULARIZATION

(71) Applicant: THE RESEARCH FOUNDATION, Albany, NY (US)

(72) Inventors: Jerome Z. Liang, Stony Brook, NY (US); Jianhua Ma, Stony Brook, NY (US); Hao Zhang, Stony Brook, NY (US); William Moore, Setauket, NY (US); Hao Han, Staten Island, NY (US)

(73) Assignee: The Research Foundation for the State University of New York, Albany, NY (US)

( * ) Notice: Subject to any disclaimer, the term of this patent is extended or adjusted under 35 U.S.C. 154(b) by 0 days.

(21) Appl. No.: 14/784,714

(22) PCT Filed: Apr. 16, 2014

(86) PCT No.: PCT/US2014/034298
§ 371 (c)(1),
(2) Date: Oct. 15, 2015

(87) PCT Pub. No.: WO2014/172421
PCT Pub. Date: Oct. 23, 2014

(65) Prior Publication Data
US 2016/0055658 A1 Feb. 25, 2016

Related U.S. Application Data

(60) Provisional application No. 61/812,506, filed on Apr. 16, 2013, provisional application No. 61/975,245, (Continued)

(51) Int. Cl.
*G06T 11/00* (2006.01)
*A61B 6/00* (2006.01)

(52) U.S. Cl.
CPC .......... *G06T 11/006* (2013.01); *A61B 6/5258* (2013.01); *A61B 6/583* (2013.01); *G06T 2211/424* (2013.01)

(58) Field of Classification Search
CPC ............. G06T 11/006; G06T 2211/424; A61B 6/5258; A61B 6/583
See application file for complete search history.

(56) References Cited

U.S. PATENT DOCUMENTS

2007/0110294 A1* 5/2007 Schaap .................... G06K 9/40
382/131
2010/0284596 A1* 11/2010 Miao ..................... G06T 11/005
382/131
(Continued)

FOREIGN PATENT DOCUMENTS

WO  WO 2005/010824  2/2005

OTHER PUBLICATIONS

Han,Guoping et al., A Fast Ray-Tracing Technique for TCT and ECT Studies, © 2000 IEEE, pp. 1515-1518.
(Continued)

*Primary Examiner* — Siamak Harandi
*Assistant Examiner* — Amandeep Saini
(74) *Attorney, Agent, or Firm* — The Farrell Law Firm, P.C.

(57) ABSTRACT

Disclosed is a method for performing X-ray Computed Tomography scanning, the method including acquiring a plurality of images of an object, obtaining an initial image from the plurality of images, calculating NonLocal weight of the initial image, utilizing a current image estimation and registered prior image, performing a successive over-relaxation optimization to yield a new image estimation with an intensity of the new image estimation equal or greater than zero, performing a cycle update, generating an image of the
(Continued)

object utilizing the new image estimation obtained from the optimization, and outputting a resultant image.

4 Claims, 15 Drawing Sheets

Related U.S. Application Data filed on Apr. 4, 2014, provisional application No. 61/975,254, filed on Apr. 4, 2014.

(56) References Cited

U.S. PATENT DOCUMENTS

| | | | |
|---|---|---|---|
| 2010/0290675 | A1 | 11/2010 | Wexler et al. |
| 2012/0105469 | A1 | 5/2012 | Pascucci |

OTHER PUBLICATIONS

Segars, W. P. et al., 4D XCAT phantom for multimodality imaging research, Med. Phys. 37 (9), Sep. 2010, © 2010 Am. Assoc. Phys. Med., pp. 4902-4915.

Buades, Antoni et al., A non-local algorithm for image denoising, Computer Vision and Pattern Recognition, 2005 CVPR 2005 IEEE Computer Society Conference on Computer Vision and Pattern Recognition, pp. 5.

Chen, Yang et al., Bayesian statistical reconstruction for low-dose X-ray computed tomography using an adaptive-weighting nonlocal prior Computerized Medical Imaging and Graphics 33 (2009) 495-500, © 2008 Elsevier Ltd., pp. 6.

Ma, Jianhua et al., Generalized Gibbs priors based positron emission tomography reconstruction, Computers in Biology and Medicine 40 (2010) 565-571, © 2010 Elsevier Ltd. pp. 7.

Wang, Zhou et al., Image Quality Assessment: From Error Visibility to Structural Similarity, IEEE Transactions on Image Processing, vol. 13, No. 4, Apr. 2004, pp. 14.

Elad, Michael et al., Image Denoising Via Sparse and Redundant Representations Over Learned Dictionaries IEEE Transactions on Image Processing, vol. 15, No. 12, Dec. 2006, pp. 3736-3745.

Fessler, Jeffrey A., Penalized Weighted Least-Squares Image Reconstruction for Positron Emission Tomography IEEE Transactions on Medical Imaging, vol. 13, No. 2, Jun. 1994, pp. 290-300, pp. 11.

Szeliski, Richard et al., Spline-Based Image Registration, International Journal of Computer Vision 22(3), 199-218 (1997), © 1997 Kluwer Academic Publishers, pp. 20.

Pati, Y. C. et al., Orthogonal Matching Pursuit: Recursive Function Approximation with Applications to Wavelet Decomposition 27th Annual Asimolar Conference on Signals Systems and Computers, Nov. 1-3, 1993, pp. 5.

Wang, Jing et al., Penalized Weighted Least-Squares Approach to Sinogram Noise Reduction and Image Reconstruction for Low-Dose X-Ray Computed Tomography IEEE Trans Med Imaging. Oct. 2006. 25(10): 1272-1283, pp. 26.

Xu, Qiong, et al., Low-Dose X-ray CT Reconstruction via Dictionary Learning, IEEE Trans Med Imaging. Sep. 2012; 31(9): 1682-1697, pp. 40.

Ma, Jianhua et al., Low-dose computed tomography image restoration using previous normal-dose scan, Med. Phys. 38 (10), Oct. 2011, © 2011 Am. Assoc. Phys. Med., pp. 19.

Ma, Jianhua et al., Iterative image reconstruction for cerebral perfusion CT using pre-contrast scan induced edge-preserving prior Phys Med Biol. Nov. 21, 2012; 57(22): 7519-7542, pp. 30.

PCT/ISA/210 Search Report issued on PCT/US2014/034298 (pp. 5).

PCT/ISA/237 Written Opinion issued on PCT/US2014/034298 (pp. 3).

Li, Tianfang et al., Reconstruction for proton computed tomography by tracing proton trajectories: A Monte Carlo study Med. Phys. 33 (3), Mar. 2006, Copyright 2006 Am. Assoc. Phys. Med., pp. 699-709.

Liang, Jerome Zhengrong et al., Proton Computed Tomography, Cancer Imaging: Instrumentation and Application. vol. 2 Elsevier: Academic Press is an imprint of Elsevier, New York, 2008, pp. 36.

\* cited by examiner

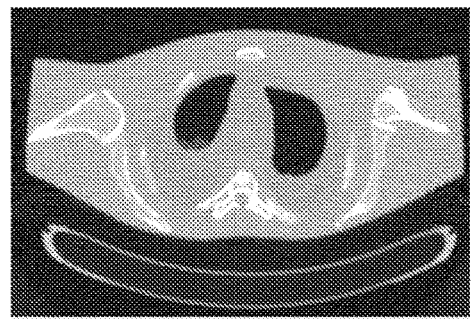
FIG.3A
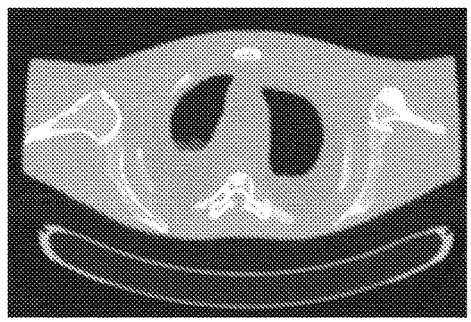 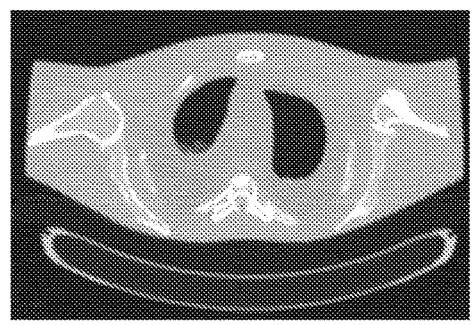
FIG.3B  FIG.3C
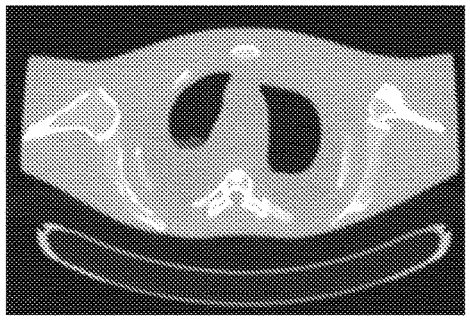 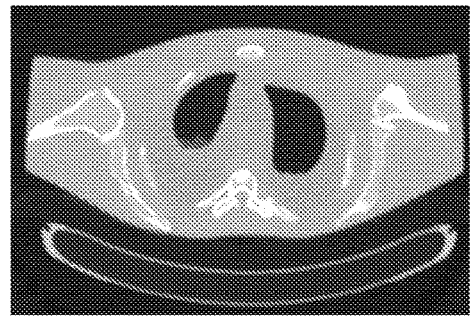
FIG.3D  FIG.3E

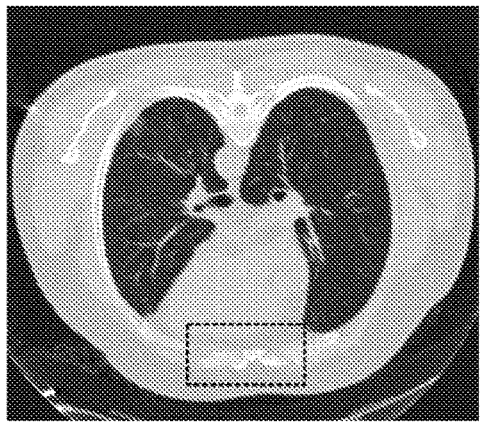
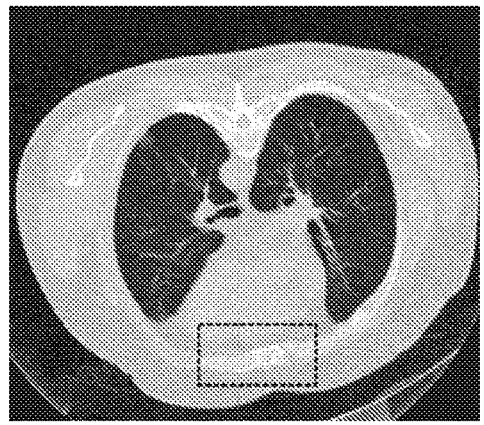
FIG.13A               FIG.13B
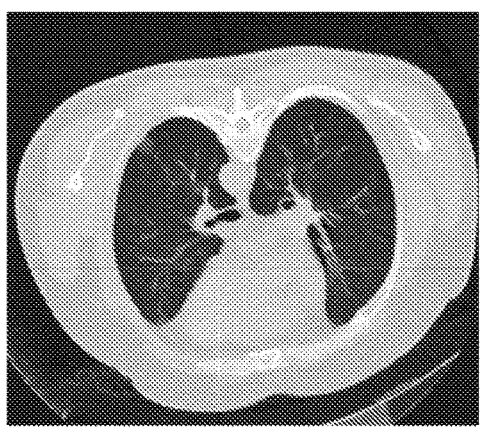
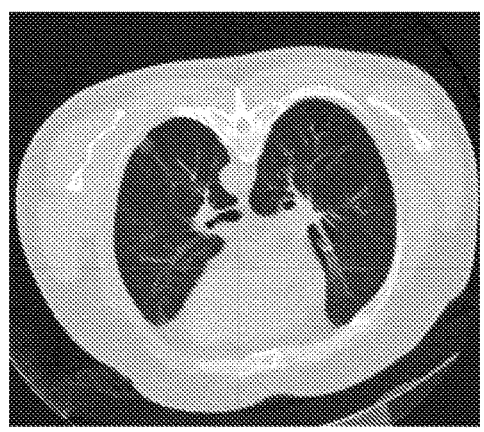
FIG.13C               FIG.13D
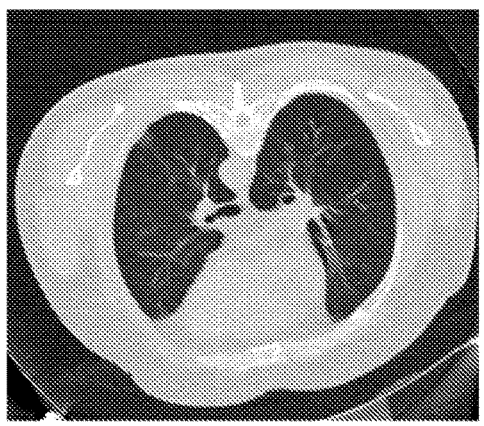
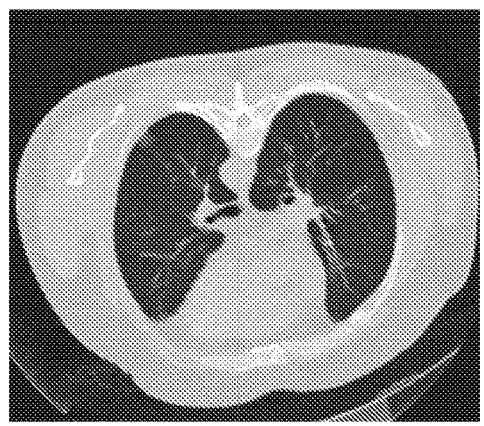
FIG.13E               FIG.13F

ITERATIVE RECONSTRUCTION FOR X-RAY COMPUTED TOMOGRAPHY USING PRIOR-IMAGE INDUCED NONLOCAL REGULARIZATION

PRIORITY

This application claims priority to U.S. Provisional Application No. 61/812,506, filed Apr. 16, 2013, to U.S. Provisional Application No. 61/975,245, filed Apr. 4, 2014, and to U.S. Provisional Application No. 61/975,254, filed Apr. 4, 2014, the contents of each of which is incorporated herein by reference.

BACKGROUND OF THE INVENTION

Field of the Invention

The present invention relates generally to medical imaging and, more specifically, to an X-ray Computed Tomography (CT) scanning device and method of operating same.

Brief Description of the Background Art

X-ray CT techniques have been widely explored and are often prescribed for clinical applications that include perfusion imaging, image-guided biopsy needle, image-guided intervention, and radiotherapy. In interventional imaging, a patient may undergo one or more imaging studies prior to acquisition of an image. In other cases, such as daily Cone Beam CT (CBCT) examinations for target localization in Image-Guided Radiation Therapy (IGRT), repeated scans are performed as a routine procedure.

The benefits of repeated CT scans are undermined by risks associated with cumulative radiation dosing, and associated patient health concerns. It is known that reducing X-ray tube current and/or shortening exposure time (mAs) in a CT scan is a simple and cost-effective method to reduce potentially harmful radiation exposure. However, the associated image will suffer from serious noise induced artifacts due to the excessive quantum noise, absent adequate treatment on noisy measurement.

Various techniques have been investigated, including optimal scan protocols and advanced image reconstruction algorithms, to reduce radiation dose in CT scans. Statistical Iterative Reconstruction (SIR) methods, which take into account statistical noise properties and accommodate imaging geometry, have shown great potential to reduce quantum noise and artifacts as compared with the current gold standard Filtered Back-Projection (FBP) reconstruction method. A major drawback of the SIR methods is the computational burden associated with multiple re-projection and back-projection operation cycles through the image domain. However, development of fast computers and dedicated hardware allow modified SIR methods to be used in advanced CT equipments.

Generally, the SIR methods can be derived from a Maximum A Posteriori (MAP) estimator given observed-data or measurement, which usually consist of two terms in an associative objective function. The first term, i.e., the data-fidelity term, models the statistical measurement. The second term, i.e., the image prior or regularization term, penalizes the solution. The data-fidelity term incorporating an accurate statistical modeling of the measurement is a prerequisite of the SIR algorithms and an edge-preserving regularization term plays an important role in successful image reconstruction. Usually, the regularization term is chosen as a shift-invariant function that penalizes the differences among local neighboring pixels. These regularizations, through equally smoothing of both noise and edge details, often tend to produce an unfavorable over-smoothing effect. In contrast to the smooth regularization, edge-preserving regularizations/priors have been proposed, e.g., the Huber prior, which replaces the quadratic penalty function with a non-quadratic penalty function that increases less rapidly compared with the quadratic penalty function for sufficiently large arguments. However, these edge-preserving regularizations/priors mostly rely on properties of local smoothness or edges, and do not consider the basic affinity structure information of a desired image, such as the gray levels, edge indicator, dominant direction, and dominant frequency.

To address the aforementioned issues of conventional regularizations/priors, an edge-preserving NonLocal (NL) prior was proposed for CT and Positron Emission Tomography (PET) image reconstructions that fully exploit density difference information, NL connectivity and continuity information of the desired image. With regard to the repeated CT scans, a previously scanned high-quality diagnostic CT image volume usually contains same anatomical information with the current scan except for some anatomical changes due to internal motion or patient weight change. Generally, the CT scans at different times are independently considered, without a systematic attempt to integrate valuable patient-specific prior knowledge, i.e., to integrate previous scanned data, which contains a wealth of prior anatomical, patient-specific information, to promote subsequent imaging process. Performing a low-dose protocol in the follow-up CT scan by fully using the previous image in the current image reconstruction framework is a topic addressed by Chen et al., which proposed a Prior Image Constrained Compressed Sensing (PICCS) algorithm to enable view angle under-sampling by integrating a prior image into the reconstruction procedure. See, *Time-Resolved Interventional Cardiac C-arm Cone-Beam CT: An Application of the PICCS Algorithm*, IEEE Trans. Med. Imaging, vol. 31, no. 4, pp. 907-923, April 2012. Lauzier extended the PICCS algorithm to the DR-PICCS algorithm for CT radiation dose reduction using a statistical model. See, *Characterization of Statistical Prior Image Constrained Compressed Sensing (PICCS): IL Application to Dose Reduction*, Med. Phys., Vol. 40, no. 2, pp. 021902:1-14, February 2013. A weakness of PICCS is that prior and current images are taken at the same global geometrical coordinates. This assumption, however, does not necessarily translate into practical settings like the IGRT applications.

Accurate registration and voxel consistency may limit wide use of the PICCS algorithm. To address this issue, Ma, et al. proposed a low-dose CT image filtering method, i.e., an ndiNLM algorithm, utilizing a high-quality normal-dose scan as priori information to perform current low-dose CT image restoration based on NL means criteria. See, J. Ma, at al, *Low-dose computed tomography image restoration using previous normal-dose scan*, Med. Phys., Vol. 38, no. 10, pp. 5713-5731, October 2011, and A. Buades, et al., *A Nonlocal Algorithm for Image Denoising*, Proc. IEEE Computer Vision and Pattern Recognition, 2005, Vol. 2, pp. 60-65. The ndiNLM algorithm performed well in noise reduction, but actually is a post-processing approach that does not consider statistical properties of the CT projection data. Another strategy that relaxes image registration is a dictionary learning based approach proposed by Xu et al., which was derived with the consideration of sparse representation theory via a sparse linear combination of the patch-based atoms in the dictionary.

SUMMARY OF THE INVENTION

To avoid the above shortcomings of conventional systems and methods, the present invention reduces radiation dosing, X-ray tube current and exposure time (mAs) during repeated CT scans, and provides a Prior-image Induced NL (PINL) regularization for statistical iterative reconstruction via Penalized Weighted Least-Squares (PWLS) criteria (PWLS-PINL). The PINL regularization utilizes redundant information in the prior-image and the Weighted Least-Squares (WLS) term considers a data-dependent variance estimation, to improve current low-dose image quality. Subsequently, a modified iterative successive over-relation algorithm is adopted to optimize the associative objective function.

The present invention also provides PINL regularization that utilizes the redundant information in the prior image and the WLS term considers a data-dependent variance estimation to improve current low-dose image quality.

An aspect of the present invention provides a method for operating an CT scanning device that includes acquiring, by the CT scanning device, a plurality of images of an object; obtaining an initial image $\mu^0$ from the plurality of images; performing a calculation of NonLocal (NL) weight utilizing a current image estimation $\mu^m$ and registered prior image $\mu_{prior}^{reg}$; performing a Successive Over-Relaxation (SOR) optimization to yield a new image estimation $\mu^{m+1}$, with an intensity of the new image estimation $\mu^{m+1}$ equal or greater than zero; performing a cycle update that repeats the obtaining of the initial image, the performing of the NL weight calculation, and the SOR optimization; generating an image of the object utilizing the new image estimation obtained from the SOR optimization; and outputting a resultant image when a stop criterion is met.

BRIEF DESCRIPTION OF THE DRAWINGS

The above and other objects, features and advantages of certain exemplary embodiments of the present invention will be more apparent from the following detailed description taken in conjunction with the accompanying drawings, in which:

FIGS. 3(a)-(e) provide anthropomorphic torso phantom reconstructions using different methods from a sinogram dataset acquired at 40 mAs, 120 kVp;

FIGS. 13(a)-(f) are clinical chest CT image reconstructions;

DETAILED DESCRIPTION OF THE PREFERRED EMBODIMENTS

Figure 1A:
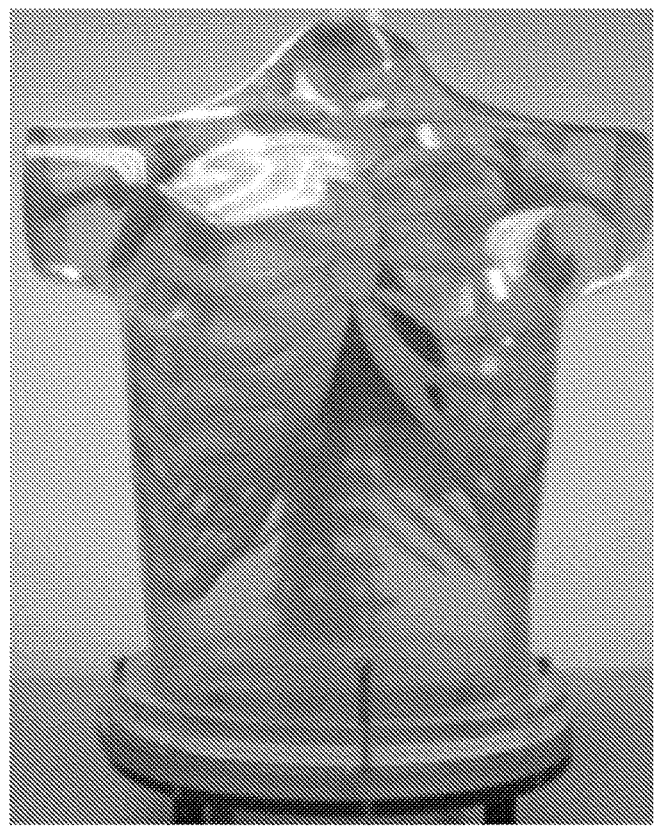
FIG. 1(a) is an anthropomorphic torso phantom utilized for experimental data acquisition by CT imaging utilizing the method of the present invention.

The following detailed description of preferred embodiments of the invention will be made in reference to the accompanying drawings. In describing the invention, an explanation about related functions or constructions known in the art are omitted for the sake of clearness in understanding the concept of the invention, and to avoid obscuring the invention with unnecessary detail.

In regards to a PWLS criteria for CT Image Reconstruction, the X-ray CT measurement can be approximately expressed as a discrete linear system according to Equation (1):

$$y = H\mu, \qquad (1)$$

where $\mu$ denotes a vector of attenuation coefficients, i.e., $\mu=(\mu_1, \mu_2, \ldots, \mu_N)'$, y represents obtained sinogram data (projections after system calibration and logarithm transformation), i.e., $y=(y_1, y_2, \ldots, y_M)'$, with "'" denoting matrix transpose, and operator H represents the system or projection matrix with a M×N size, and $H_{ij}$ denotes the length of intersection of projection ray i with pixel j. In a preferred embodiment, the associated element is pre-calculated by a fast ray-tracing technique, See, G. Han, et al., *A Fast Ray-Tracing Technique for TCT and ECT Studies*, in Proc. IEEE NSS-MIC, Seattle, Wash., 1999, Vol. 3, pp. 1515-1518, and stored as a file. The goal of CT image reconstruction is to estimate the attenuation coefficients $\mu$ from measurement y.

According to the measurement model of Equation (1) and MAP estimation criterion, the mathematical formula for PWLS image reconstruction with a regularization term $R(\mu)$ is expressed by Equation (2):

$$\mu^* = \arg\min_{\mu \geq 0} \{(y - H\mu)'\Sigma^{-1}(y - H\mu) + \beta R(\mu)\}, \qquad (2)$$

where $\Sigma$ is a diagonal matrix with the ith element of $\sigma_i^2$ which is the variance of sinogram data y, and $\beta$ is a hyper-parameter that controls strength of regularization.

To determine parameter $\sigma_i^2$ in Equation (2), several methods can be used. See, Wang, et al., *Penalized weighted least-squares approach to sinogram noise reduction and image reconstruction for low-dose X-ray computed tomography*, IEEE Trans. Med. Imaging, Vol. 25, no. 10, pp.

1272-1283, October 2006, and Xu, et al., *Low-dose X-ray CT Reconstruction via Dictionary Learning*, IEEE Trans. Med. Imaging, Vol. 31, no. 9, pp. 1682-1697, September 2012. In an embodiment of the present invention, the variance of $\sigma_i^2$ was determined by the mean-variance relationship proposed by Ma, et al., written as Equation (3):

$$\sigma_i^2(y) = \frac{1}{I_0}\exp(\overline{p}_i)\left(1 + \frac{1}{I_0}\exp(\overline{p}_i)(\sigma_e^2 - 1.25)\right), \quad (3)$$

where $I_0$ denotes incident X-ray intensity, $\overline{p}_i$ is the mean of sinogram data y at bin i, and $\sigma_e^2$ is the background electronic noise variance.

In regards to providing an overview of PINL regularization, traditionally, $R(\mu)$ in Equation (2) is designed by a simple weighted sum of potential function on difference values of neighboring pixels in image domain, see Wang, et al., and can be described as Equation (4):

$$R(\mu) = \sum_j R(\mu_j) = \sum_j \sum_{k \in S_j} w(k, j)\varphi(\mu_j - \mu_k), \quad (4)$$

where index j runs over all image elements in the image domain, $S_j$ represents a local neighborhood of the jth image pixel in two dimensions, $\varphi$ denotes a convex and positive potential function satisfying $\varphi(0)=0$, and weight $w(k, j)$ is positive and symmetric, i.e., $w(k, j) \geq 0$ and $w(k, j)=w(j, k)$, which are usually designed as an inverse proportion of the distance between pixels k and j in $S_j$, with the regularizations being local for lack of global connectivity or continuity.

In repeated CT scans, a previously scanned normal-dose CT image has a lower noise level and higher resolution compared to a current low-dose CT image, with a majority of the anatomical information being the same between the two scans. Thus, to fully utilize the redundancy of information in the prior image, a PINL regularization is utilized with a quadratic potential function, as according to Equation (5):

$$R_{PINL}(\mu) = \sum_j \sum_{k \in N_j} w(k, j)(\mu_j - \mu_{prior,k}^{reg})^2, \quad (5)$$

where $\mu_{prior}^{reg}$ denotes a registered prior image between prior image $\mu_{prior}$ and current low-dose image $\mu$, and $N_j$ denotes a search-window in image $\mu_{prior}^{reg}$.

NL weight $w(k, j)$ between the prior image and the current objective image is provided by Equations (6)-(8):

$$w(k, j) = \exp(-D(k, j)/h^2) \Big/ \sum_{k \in N_j} \exp(-D(k, \overline{j})/h^2), \quad (6)$$

$$D(k, j) = \|\mu(n_j) - \mu_{prior}^{reg}(n_k)\|_2^2, \quad (7)$$

$$\mu(n_j) = \{\mu_l : l \in n_j\}, \quad (8)$$

$$\mu_{prior}^{reg}(n_k) = \{\mu_{prior,l}^{reg} : l \in n_k\},$$

with weight $w(k, j)$ being a decreasing function of similarity between two local neighborhoods $n_k$ and $n_j$, i.e., patch-windows, centered at pixel k in image domain $\mu_{prior}^{reg}$ and pixel j in image domain $\mu$, respectively; $\|\cdot\|_2^2$ representing 2D Euclidean distance between two similarity patch-windows; $\mu(n_j)$ and $\mu_{prior}^{reg}(n_k)$ denoting vector of neighborhood pixel values restricted in patch-windows $n_j$ and $n_k$, respectively; and h being a parameter that controls exponential function decay.

The objective function of PWLS with the present PINL regularization, i.e., PWLS-PINL, for CT image reconstruction can be rewritten as Equation (2), above.

In regards to implementation of the PWLS-PINL method, the current CT images and the initial high-dose CT images are first reconstructed by the FBP method, and then a B-spline based image registration technique, see R. Szeliski, et al., Spline-Based Image Registration, International Journal of Computer Vision, Vol. 22, no. 3, pp. 199-218, 1997, is adopted to generate the registered prior image from the initial high-dose CT image, with the effectiveness of the B-spline based image registration algorithm having been extensively validated by numerous registration experiments. Based on the transformation matrix, all voxels of the prior CT images are then transformed into the current CT images to obtain globally aligned prior images. Similar to previous studies in low-dose CT image restoration, see Ma, et al., through two roughly aligned images, the rich redundant information in the prior image can be effectively used to induce the PINL regularization for low-dose image reconstruction, as described below.

After obtaining the registered prior image $\mu_{prior}^{reg}$, weight $w(k, j)$ in Equation (6) is regarded as a function of current estimation $\mu$ and registered prior image $\mu_{prior}^{reg}$. Because of nonlinearity in calculating weight $w(k, j)$, minimizing the objective function of Equation (9) is difficult for a closed-solution. To address this problem, a binary optimal scheme is used to minimize the objective function of Equation (9). See, J. Ma, et al, *Generalized Gibbs Priors Based Positron Emission Tomography Reconstruction*, Comput. Biol. Med., Vol. 40, no. 6, pp. 565-571, June 2010, and J. Ma, et al., *Iterative Image Reconstruction for Cerebral Perfusion CT Using a Pre-contrast Scan Induced Edge-preserving Prior*, Phys. Med. Biol., Vol. 57, no. 22, pp. 7519-7542, November 2012. Specifically, weight $w(k, j)$ is automatically adjusted according to the similarity between patch-windows in current estimation $\mu^n$, with n as an iterative index, and the registered prior-image $\mu_{prior}^{reg}$ during each iteration.

The iterative successive over-relaxation algorithm of J. Wang, et al., and J. A. Fessler, *Penalized Weighted Least-squares Image Reconstruction for Positron Emission Tomography*, IEEE Trans. Med. Imaging, Vol. 13, no. 2, pp. 290-300, 1994, is modified to calculate the solution of Equation (2). In the implementation, the variance $\sigma_i^2$, i.e., the element of weight matrix in Equation (2), is updated in each iteration according to Equation (3) to more accurately estimate the sinogram variance, with the implementation referred to herein as an PWLS-PINL algorithm, with presented PWLS-PINL algorithm summarized in Table 1.

TABLE 1

1: initial: $\mu_j^0$ = FBP{y}; j = 1, 2, 3, . . . , N; m = 0;
2: while (stop criterion is not met)
3:     for each pixel j in image $\mu$, (Nonlocal weight calculation)
4:     D(k, j) = $\|\mu(n_j) - \mu_{prior}^{reg}(n_k)\|_2^2$;
5:

$$w^m(k, j) = \exp\{-D(k, j)/h^2\} \Big/ \sum_{k \in N_j} \exp\{-D(k, j)/h^2\};$$

6:     end for
7:     $r^m := y - H \mu^m$;
8:     $\Sigma := \text{diag}(\sigma^2(H \mu^k))$;

TABLE 1-continued

9: $S_j := H_j^T \Sigma^{-1} H_j, \forall j;$
10:     for each pixel j, (Successive over-relaxation optimization)
11: $$\tilde{\mu}_j^{m+1} = \frac{H_j^T \Sigma^{-1} r^m + S_j \mu_j^m + \beta \sum_{k \in N_j} w(k,j) \mu_{prior,k}^{reg}}{S_j + \beta \sum_{k \in N_j} w(k,j)};$$
12:     $\mu_j^{m+1} = \max\{0, (1-\omega)\mu_j^m + \omega \tilde{\mu}_j^{m+1}\};$
13: end for
14: calculate the criterion;
15: m := m + 1;
16: end if stop criterion is satisfied In Table 1, a two-hundredth iterated image was selected as a result corresponding to a stable estimation without visually changing further iterations.

Figure 1B:
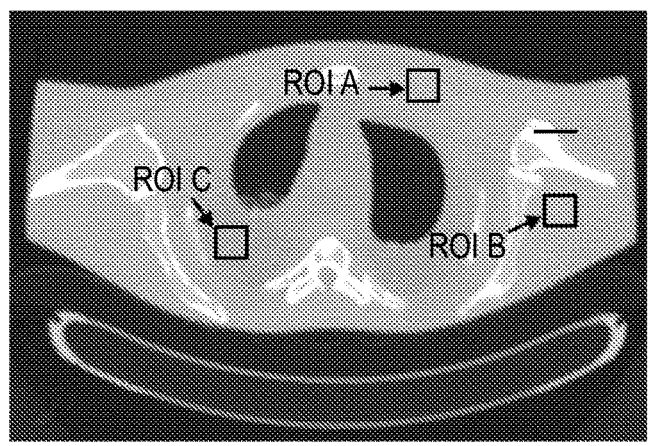
FIG. 1(b) shows a CT image reconstructed by Filtered Back-Projection (FBP) reconstruction with an optimized Hamming filter from sinogram data acquired at 100 mAs, 120 kVp.

FIGS. 1(a)-1(b) are provided in regards to data acquisition, with FIG. 1(a) showing an anthropomorphic torso phantom (Radiology Support Devices, Inc., Long Beach, Calif.) utilized for experimental data acquisition by CT imaging utilizing the method of the present invention. The phantom of FIG. 1(a) was scanned by a clinical CT scanner, i.e., Siemens SOMATOM Sensation 16 CT, at three exposure levels, i.e., 17, 40, 100 mAs. For each exposure level, the tube voltage was set at 120 kVp and the phantom was scanned in a Cine mode at a fixed bed position.

FIG. 1(b) shows the CT image reconstructed by the Filtered Back-Projection (FBP) reconstruction method with an optimized Hamming filter from the sinogram data acquired at 100 mAs, 120 kVp. The deformed images were simulated by mechanically performing a cosine transform warped distortion on images reconstructed by the FBP method from the sinogram data acquired at 100 mAs, 120 kVp. To obtain the registered prior images, the deformed image volume was registered to the images reconstructed by the FBP method from the sinogram data acquired at 17 and 40 mAs, respectively.

To evaluate the influence of mismatch between the prior and current images on the performance of the PWLS-PINL and PICCS methods, an XCAT phantom was used to simulate the normal-dose and low-dose CT image volumes with the same anatomical structures. See, W. Segars, et al., 4D XCAT Phantom for Multimodality Imaging Research, Med. Phys., vol. 37, no. 9, pp. 4902-4915, September 2010. The associated projection data were simulated using a CT simulator at two exposure levels, i.e., 232 and 23.2 mAs. For each exposure level, tube voltage was set at 120 kVp, time per gantry rotation at 1.0 s, and slice thickness at 3.0 mm. The system geometry represented a system with 1,800 mm source-to-detector distance, 1510.4 mm center-to-source distance, and 0.8448 mm detector pixels (672 radial bins). Reconstructions were made on an image volume of size 512×512×100.

Patient experimental data were obtained with patient consent for chest CT study, with the experimental data acquired by the Siemens SOMATOM Sensation 16 CT scanner, with scanning parameters of 1.0 mm pitch, gantry rotation of 0.5 seconds, slice thickness of 5.0 mm, tube voltage of 120 kVp, and tube currents of 40 and 400 mA.

An evaluation was performed utilizing metrics to evaluate noise reduction on the reconstructed image from the low-dose sinogram data with Signal to Noise Ratio (SNR); local Signal to Noise Ratio (lSNR); and relative Root Mean Square Error (rRMSE) provided by Equations (9)-(11):

$$SNR = 10 \log_{10} \left( \frac{\sum_{m=1}^{Q} (\mu_m - \bar{\mu})^2}{\sum_{m=1}^{Q} (\mu_m - \mu_{GS,m})^2} \right), \quad (9)$$

$$lSNR = \frac{\frac{1}{Q}\sum_{m=1}^{Q} \mu_m}{\sqrt{\frac{1}{Q}\sum_{m=1}^{Q}\left(\mu_m - \frac{1}{Q}\sum_{m=1}^{Q}\mu_m\right)^2}}, \quad (10)$$

$$rRMSE = \sqrt{\frac{\sum_{m=1}^{Q} |\mu_m - \mu_Q|^2}{\sum_{m=1}^{Q} |\mu_{GS,m}|^2}}, \quad (11)$$

where $\mu$ represents the reconstructed image from the low-dose sinogram data, $\mu_{GS}$ denotes a golden standard image, m indicates the voxel index in the ROI, Q is the number of voxels in the ROI, and $\bar{\mu}$ denotes the mean voxel value in the ROI, with the golden standard image being reconstructed by the FBP method with ramp filer from the averaged sinogram data of 150 times repeated scans at 100 mAs, 120 kVp.

To explore the performance of the various algorithms at the local detail level, the Universal Quality Index (UQI) was utilized to conduct an ROI based analysis by evaluating the degree of similarity between the reconstructed and golden standard images. See, Z. Wang, et al., Image Quality Assessment: From Error Visibility to Structural Similarity, IEEE Trans. Image Process., Vol. 13, no. 4, pp. 600-612, April 2004. Given a selected ROI at corresponding locations in the two images, the mean, variance and covariance of intensities in the ROI were respectively calculated according to Equations (12)-(14):

$$\bar{\mu} = \frac{1}{Q}\sum_{m=1}^{Q} \mu_m, \quad (12)$$

$$\sigma^2 = \frac{1}{Q-1}\sum_{m=1}^{Q} (\mu_m - \bar{\mu})^2$$

$$\bar{\mu}_{GS} = \frac{1}{Q}\sum_{m=1}^{Q} \mu_{GS,m}, \quad (13)$$

$$\sigma_{GS}^2 = \frac{1}{Q-1}\sum_{m=1}^{Q} (\mu_{GS,m} - \bar{\mu}_{GS})^2$$

$$\text{cov}(\mu, \mu_{GS}) = \frac{1}{Q-1}\sum_{m=1}^{Q} (\mu_m - \bar{\mu})(\mu_{GS,m} - \bar{\mu}_{GS}), \quad (14)$$

where $\mu_{GS}$ denotes a golden standard image, m is the voxel index, and Q denotes the number of voxels within the ROI. Then, the UQI can be calculated according to Equation (15):

$$UQI = \frac{2\,\text{cov}(\mu, \mu_{GS})}{\sigma^2 + \sigma_{GS}^2} \frac{2\bar{\mu}\bar{\mu}_{GS}}{\bar{\mu}^2 + \bar{\mu}_{GS}^2}. \quad (15)$$

UQI measures the intensity similarity between the two images, with the UQI value ranging from zero to one. A UQI value closer to one suggests better similarity to the golden standard image.

Evaluation by Contrast-to-Noise Ratio (CNR). For quantitative evaluation of the reconstruction images, two different ROIs were selected, as discussed in regards to Table 4, below, for calculation of the CNR, which is defined in Equation (16):

$$CNR = \frac{|\bar{\mu}_{ROI} - \bar{\mu}_{BG}|}{\sqrt{\sigma_{ROI}^2 + \sigma_{BG}^2}}, \qquad (16)$$

where $\bar{\mu}_{ROI}$ is the mean of the voxels inside the ROI, $\bar{\mu}_{BG}$ is the mean of the voxels in the background, and $\sigma_{ROI}$ and $\sigma_{BG}$ are standard deviations of voxel values inside the ROI and the background region, respectively.

In regards to comparison methods, to validate and evaluate the performance of the present PWLS-PINL method, the FBP method using ramp filter, the NL-prior based PWLS (PWLS-NL) method (See J. Ma, et al., Y. Chen, et al., *Bayesian Statistical Reconstruction for Low-Dose X-ray Computed Tomography Using an Adaptive-Weighting Nonlocal Prior*, Comput. Med. Imaging Graph., Vol. 33, no. 7, pp. 495-500, October 2009, the PICCS method, G. H. Chen, et al., P. Lauzier et al., and a Global Dictionary based Statistical Iterative Reconstruction (GDSIR) approach of Q. Xu, et al.), were adopted for comparison. The NL-prior term in the PWLS-NL approach is expressed as Equation (17):

$$R_{NL}(\mu) = \sum_j \sum_{k \in N_j} w(k, j)(\mu_j - \mu_k)^2, \qquad (17)$$

wherein weigh w(k, j) is defined by Equations (18)-(19):

$$w(k,j) = \exp(-\|\mu(n_j) - \mu(n_k)\|_2^2 / h^2), \qquad (18)$$

$$\mu(n_j) = \{\mu_l | l \in n_j\}, \mu(n_k) = \{\mu_l | l \in n_k\}, \qquad (19)$$

where $n_j$ and $n_k$ represent patch-windows, and $N_j$ denotes a search-window in a current low-dose CT image domain.

The PICCS algorithm under the PWLS framework can be formulated as Equation (20):

$$\mu^* = \arg\min_{\mu \geq 0}[\alpha\|\psi_1(\mu - \mu_{prior})\|_1 + (1-\alpha)\|\psi_2(\mu)\|_1] + \qquad (20)$$
$$\frac{\lambda}{2}(y - H\mu)'\Sigma^{-1}(y - H\mu).$$

$\mu_{prior}$ is the prior image, $\psi_1$ and $\psi_2$ are sparsifying transforms, $\alpha \in [0,1]$ is a scalar that controls the relative weights to be allocated to the prior image and Compressing Sensing (CS) terms, and $\|x\|_1$ represents the $l_1$-norm defined as $$\|x\|_1 = \sum_i |x_i|.$$

In the implementation, the sparsifying transform used for both $\psi_1$ and $\psi_2$ is the image spatial gradient norm, which is also equivalent to a Total Variation (TV). See T. Lauzier, et al.

The GDSIR is a patch based approach that extracts the prior information via a global dictionary trained from a high-quality image, and the associative image reconstruction is equivalent to solve the minimization problem of Equation (21):

$$\{\mu^*, \alpha^*\} = \arg\min_{\mu,\alpha}(y - H\mu)'\Sigma^{-1}(y - H\mu) + \qquad (21)$$
$$\gamma\left(\sum_s \|E_s\mu - D\alpha_s\|_2^2 + \sum_s \upsilon_s \|\alpha_s\|_0\right),$$

where $D \in \Re^{N \times K}$ represents a trained dictionary whose column $d_k \in \Re^{N \times 1}$ (k=1, ..., K) is a N dimensional vector, $\alpha_s \in \Re^{K \times 1}$ is a representation vector with few nonzero entries, $\|\cdot\|_0$ denotes the $l_0$-norm, $E_s \in \Re^{K \times K}$ is the matrix to extract a patch from the image $\mu$, $\upsilon_s$ is a Lagrange multiplier, and $\gamma$ is a hyper-parameter. In a preferred embodiment, a global dictionary with a size of 64×256, (N=8×8, K=256) was generated from a normal-dose prior image by using a KSVD algorithm wherein an Orthogonal Matching Pursuit (OMP) technique was used for sparse representation. See, M. Elad, et al., *Image Denoising via Sparse and Redundant Representations Over Learned Dictionaries*, IEEE Trans. Image Process., vol. 15, no. 12, pp. 3736-3745, December 2006, and Y. C. Pati, et al., *Orthogonal Matching Pursuit: Recursive Function Approximation With Applications to Wavelet Decomposition*, in Proc. 27th Asilomar Conf. Signals Syst. Comput., Pacific Grove, C A, 1993, Vol. 1, pp. 40-44. Additionally, an alternating minimization scheme of Q. Xu et al. was adapted to find the solution of Equation (21), above.

Results of an anthropomorphic torso phantom study utilizing the method of the present invention are as follows.

In regards to noise and artifacts suppression, FIGS. 2(a)-(e) and 3(a)-(e) show results reconstructed by five different methods from sonogram data acquired at 17 and 40 mAs, respectively.

Figure 2A:
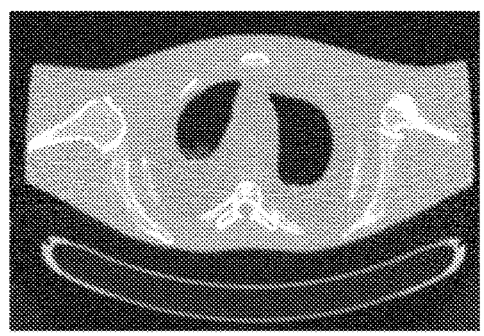
FIGS. 2(a)-(e) provide anthropomorphic torso phantom reconstructions using different methods from a sinogram dataset acquired at 17 mAs, 120 kVp.
Figure 2B:
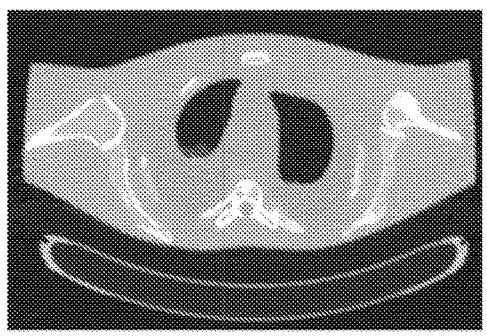
Figure 2C:
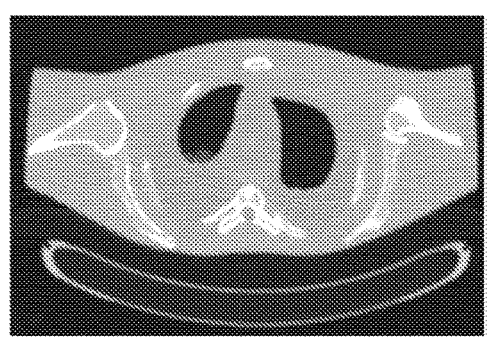
Figure 2D:
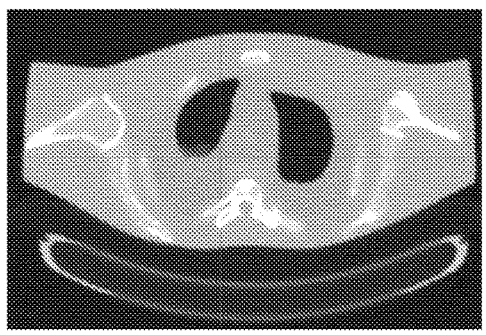
Figure 2E:
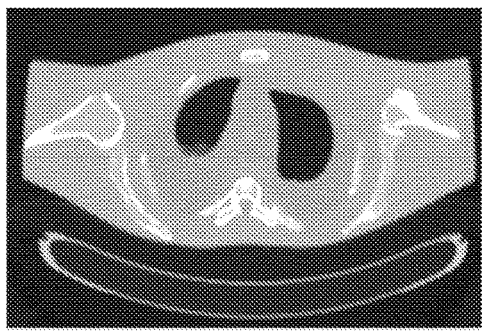

In FIGS. 2(a)-(e), the anthropomorphic torso phantom reconstructions are provided using different methods from the sinogram dataset acquired at 17 mAs, 120 kVp; with FIG. 2(a) utilizing FBP reconstruction with ramp filter; FIG. 2(b) utilizing PWLS-NL reconstruction (N=21×21, n=5×5, h=2.0×10$^{-3}$, β=2.5×10$^4$); FIG. 2(c) utilizing PICCS reconstruction (α=0.6, λ=0.1); (d) the image reconstructed by the GDSIR method (γ=4×10$^{-2}$) with a global dictionary trained from the prior image of FIG. 1(b); and FIG. 2(e) showing the PWLS-PINL reconstruction (N=21×21, n=5×5, h=2.0×10$^{-3}$, β=2.0×10$^4$), with all images displayed in a same window. FIGS. 3(a)-(e) provide anthropomorphic torso phantom reconstructions using four different methods from the sinogram dataset acquired at 40 mAs, 120 kVp; with FIG. 3(a) using the FBP reconstruction with ramp filter; FIG. 3(b) using the PWLS-NL reconstruction (N=21×21, n 5×5, h=2.0×10$^{-3}$, β=2.5×10$^4$); FIG. 3(c) using the PICCS reconstruction using FIG. 1(b) as the prior image (α=0.6, λ=0.12); FIG. 3(d) using the image reconstructed by the GDSIR method (γ=3×10$^{-2}$); and FIG. 3(e) using the PWLS-PINL reconstruction using FIG. 1(b) as the prior image (N=21×21, n=5×5, h=2.0×10$^{-3}$, β=2.0×10$^4$), with all images displayed in a same window.

In more detail, FIGS. 2(a) and 3(a) show images reconstructed by the FBP method with a ramp filter, with noticeable noise-induced streak artifacts being observed. FIGS. 2(b) and 3(b) show the images reconstructed by the PWLS-NL method. The noise was mostly suppressed, but undesired streak artifacts are still observed in highly attenuated regions, partially because properties of NL weight calculations for structuring preservation. FIGS. 2(c) and 3(c) show images reconstructed by the PICCS method using FIG. 1(b) as the prior image. The PICCS method can yield reasonable images with sharp edges. Further, the smooth regions are plagued by some streak artifacts, which may have resulted from the TV processing. In the context of medical imaging, this noise might result in deceptive structures. FIGS. 2(d) and 3(d) show images reconstructed by the GDSIR method wherein the global dictionary was trained from the normal-dose image FIG. 1(b). It can be seen that some distortions occurred in the case of 17 mAs while satisfactory result appeared with noticeable noise reduction in the case of 40 mAs. FIGS. 2(e) and 3(e) show the images reconstructed by the present PWLS-PINL method wherein the prior image is the same as that used in the PICCS and GDSIR methods. The PWLS-PINL method achieves more gains over the PICCS and GDSIR methods in terms of successful noise-induced artifacts suppression and edges detail preservation.

Figure 4A:
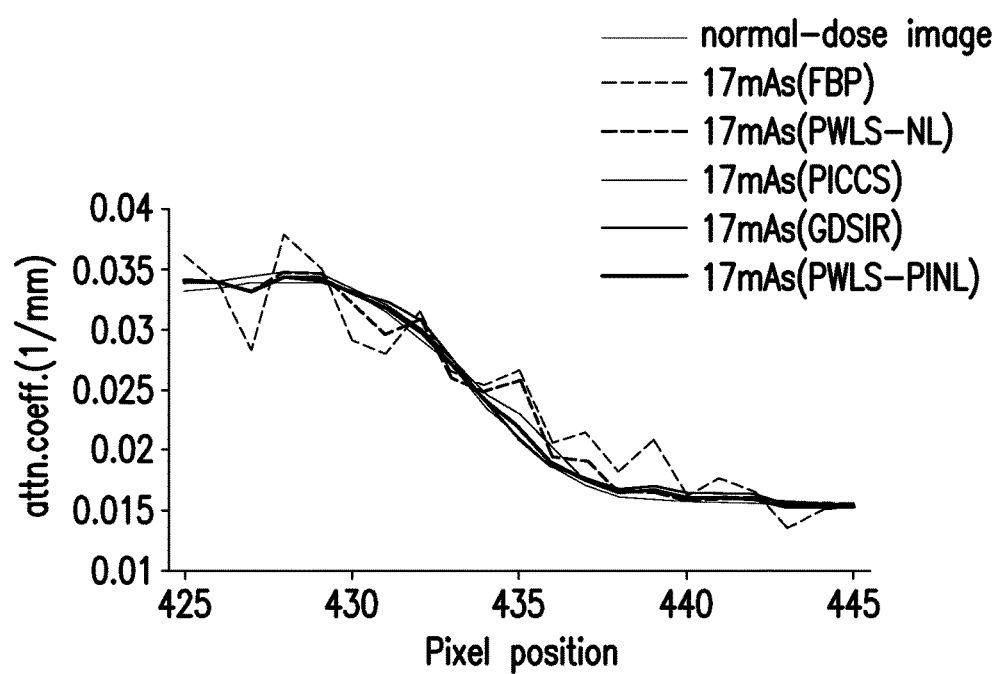
FIGS. 4(a)-(b) are graphs of horizontal profiles located at voxel position y=227 and x from 425 to 445, at line in FIG. 1(b)
Figure 4B:
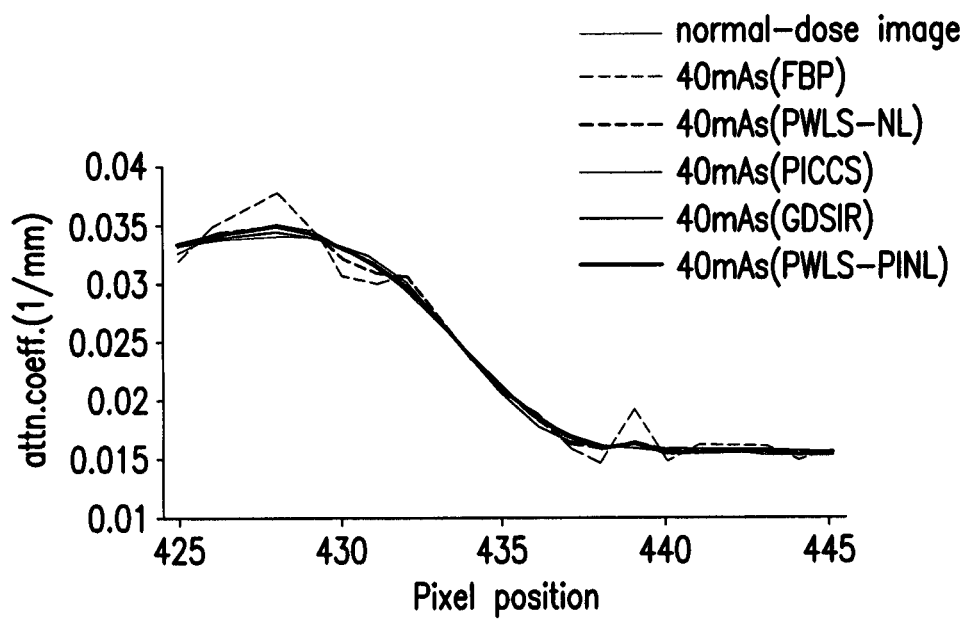

FIGS. 4(a)-4(b) are graphs of the associated horizontal profiles located at the voxel position y=277 and x from 425 to 445, as indicated by the line in the upper right portion of FIG. 1(b). FIG. 4(a) graphs different reconstructions in FIGS. 2(a)-(e) in the case of 17 mAs, and FIG. 4(b) graphs different reconstruction in FIGS. 3(a)-(e) in the case of 40 mAs. The profiles from the present PWLS-PINL method agree much better with those from the normal-dose scan, compared with conventional methods.

To quantitatively evaluate the PWLS-PINL method, the lSNR and rRMSE of the three different ROIs, as indicated by the squares in FIG. 1(b), were measured in the two cases of 17 and 40 mAs, and are summarized in Tables 2 and 3. All statistical model based methods, i.e., the PWLS-NL, PICCS, GDSIR and PWLS-PINL, yielded more gains over the FBP reconstructions from the same sinogram data in terms of the lSNR and rRMSE measures in the three different ROIs. The results partially demonstrate that the present PWLS-PINL method achieves noticeable gains over the other methods in terms of noise and artifacts suppression. However, the PICCS method is superior to the present PWLS-PINL algorithm in terms of the lSNR and rRMSE measures in the matched region of ROIA due to the strong same information from the prior image incorporated into the reconstructed image.

Image quality metrics on the three ROIs indicated by the squares in FIG. 1(b) for the case of 17 mAs are provided in Table 2.

TABLE 2

| Methods | ROI A | | ROI B | | ROI C | |
|---|---|---|---|---|---|---|
| | lSNR | rRMSE | lSNR | rRMSE | lSNR | rRMSE |
| FBP | 8.66 | 0.1158 | 5.64 | 0.1783 | 4.94 | 0.2078 |
| PWLS-NL | 76.56 | 0.0157 | 62.25 | 0.0181 | 36.61 | 0.0310 |
| PICCS | 96.80 | 0.0116 | 50.74 | 0.0213 | 15.87 | 0.0674 |
| GDSIR | 48.83 | 0.0224 | 38.75 | 0.0272 | 27.49 | 0.0407 |
| PWLS-PINL | 76.72 | 0.0156 | 62.19 | 0.0181 | 44.31 | 0.0266 |

Image quality metrics on the three ROIs as indicated by the squares in FIG. 1(b) in the case of 40 mAs are provided in Table 3.

TABLE 3

| Methods | ROI A | | ROI B | | ROI C | |
|---|---|---|---|---|---|---|
| | lSNR | rRMSE | lSNR | rRMSE | lSNR | rRMSE |
| FBP | 15.05 | 0.0654 | 9.15 | 0.1090 | 9.05 | 0.1100 |
| PWLS-NL | 89.25 | 0.0126 | 59.77 | 0.0179 | 52.84 | 0.0205 |
| PICCS | 106.18 | 0.0043 | 91.55 | 0.0138 | 54.99 | 0.0177 |
| GDSIR | 98.45 | 0.0115 | 74.11 | 0.0153 | 59.10 | 0.0190 |
| PWLS-PINL | 101.54 | 0.0114 | 72.96 | 0.0155 | 61.20 | 0.0183 |

Figure 5:
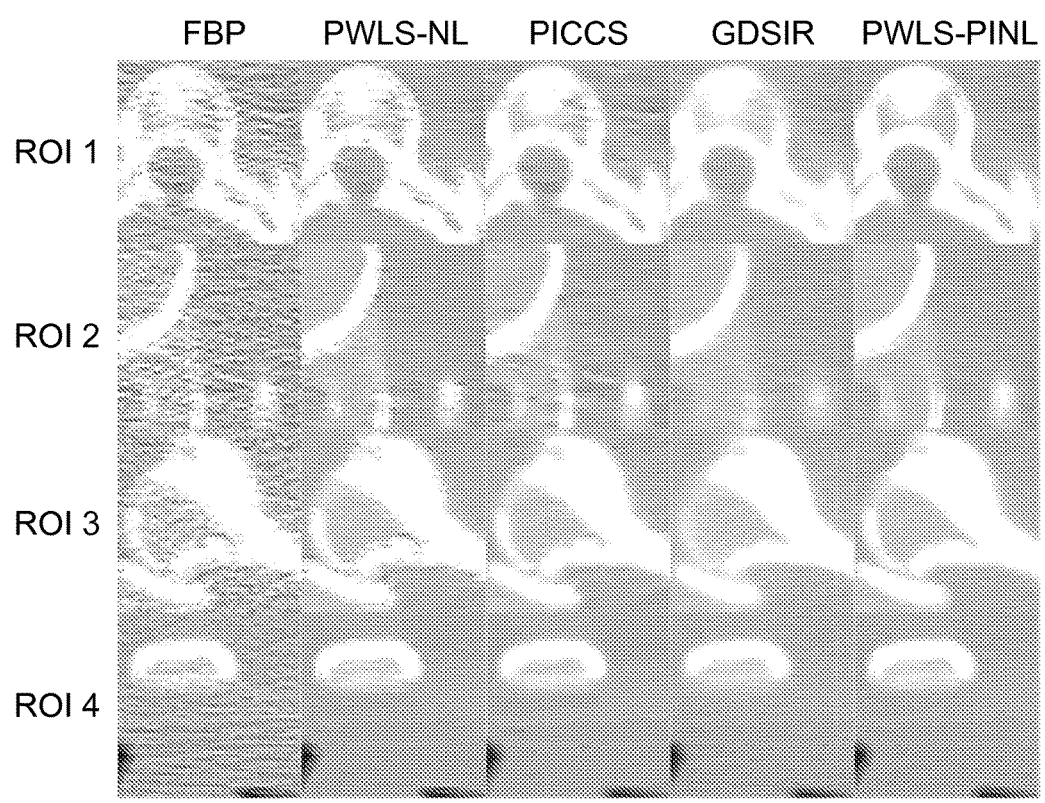
FIG. 5 provides zoomed details of four Regions Of Interest (ROIs) of FIGS. 2(a)-(e)
Figure 6:
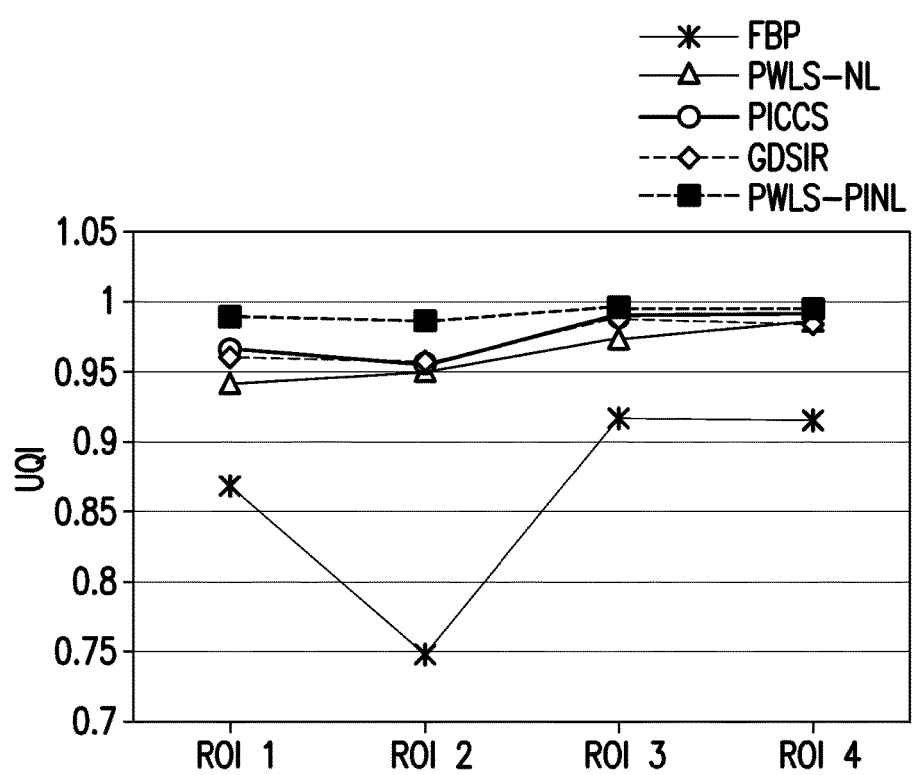
FIG. 6 is a graph of Universal Quality Index (UQI) measures for the ROIs of FIG. 5.
Figure 7:
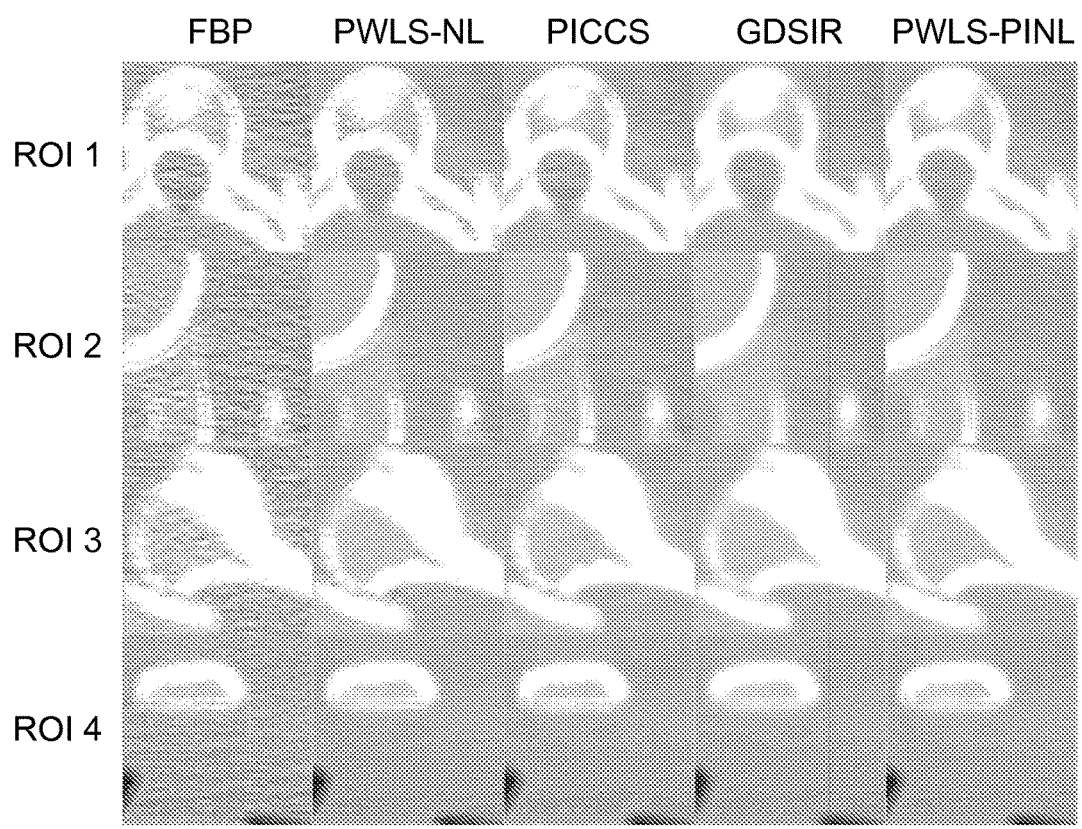
FIG. 7 provides zoomed details of four ROIs of FIGS. 3(a)-(e)
Figure 8:
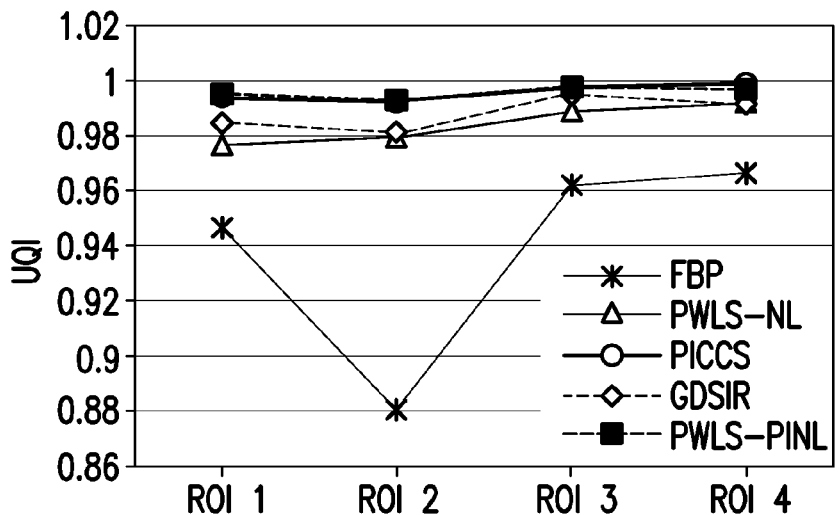
FIG. 8 is a graph of UQI measures for the ROIs of FIG. 7.

For the UQI measure, FIGS. 5 and 7 show zoomed details of the four ROIs in FIGS. 2(a)-(e) and 3(a)-(e), respectively. The PWLS-PINL method achieves significant gains over other methods in terms of the resolution preservation. The corresponding UQI scores are shown in FIGS. 6 and 8, respectively. The PWLS-PINL method yields higher UQI scores (more than 0.98) than the other methods, in both cases of 17 and 40 mAs.

Figure 16:
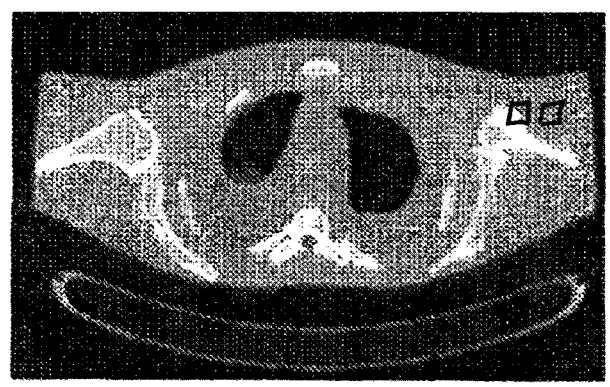

FIG. 16 provides an anthropomorphic torso phantom reconstruction showing squares of CNR measurement of images. Table 4 provides CNR measurements of images reconstructed by the four different methods from the sonogram data at 17 and 40 mAs. The ROIs for the CNR measure are marked by the two squares in located at the top left corner of FIG. 16, showing that the present PWLS-PINL method achieves significant ability for region contrast identification, which is very important for low-dose CT image reconstruction.

TABLE 4

| | FBO | PWLS-NL | PICCS | GDSIR | PWLS-PINL |
|---|---|---|---|---|---|
| 17 mAs | 4.9263 | 16.3171 | 19.1611 | 22.1908 | 25.7145 |
| 40 mAs | 6.8687 | 22.8748 | 20.4515 | 25.8076 | 27.2561 |

In regards to convergence analysis of the PWLS-PINL algorithm, to validate and analyze the convergence of the present PWLS-PINL method, global rRMSE and SNR measures on the entire to-be-reconstructed anthropomorphic torso phantom image were performed.

Figure 9A:
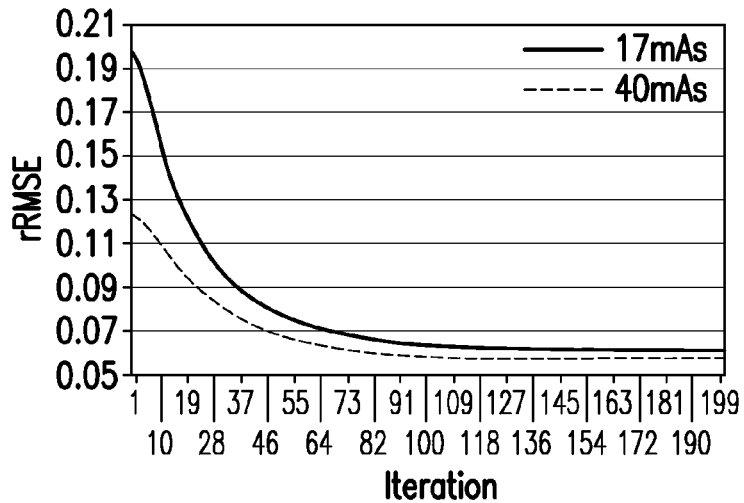
FIG. 9(a) is a graph of a global relative Root Mean Square Error (rRMSE) of the PWLS-PINL method of the present invention.
Figure 9B:
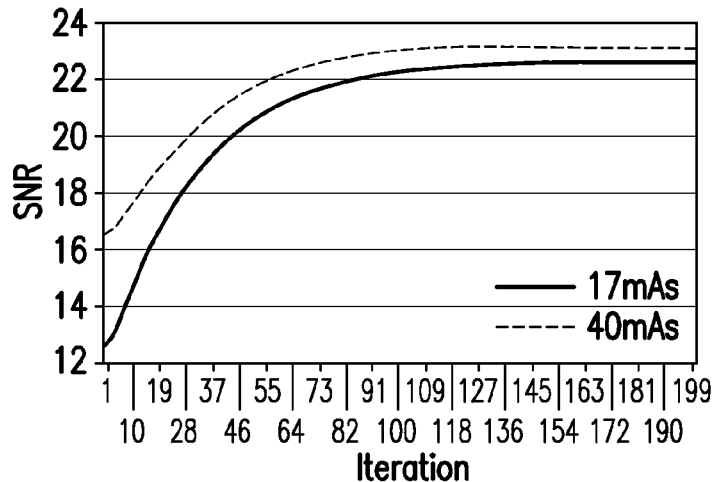
FIG. 9(b) is a graph of a global Signal to Noise Ratio (SNR) of the PWLS-PINL method of the present invention.

FIG. 9(a) is a graph of a global rRMSE of the present PWLS-PINL method by number of iterations, and FIG. 9(b) is a graph of a global SNR of the present PWLS-PINL method by number of iterations, from anthropomorphic torso phantom reconstructions in the two cases of 17 mAs and 40 mAs. FIGS. 9(a)-(b) show the rRMSE and SNR measures with respect to the number of iterations in the two cases of 17 and 40 mAs, showing a result that the present PWLS-PINL algorithm yields a steadily convergence solution in terms of the global rRMSE and SNR measurements.

In regards to influence of image registration accuracy on the PWLS-PINL method, to evaluate the influence of the image registration accuracy on the performance of the PWLS-PINL method, an elastically deformed FBP image was used from the original image reconstructed from the sinogram data acquired at 100 mAs, 120 kVp and the corresponding registered image by the B-spline based registration algorithm as the prior images to induce image reconstruction by the PWLS-PINL method.

Figure 10A:
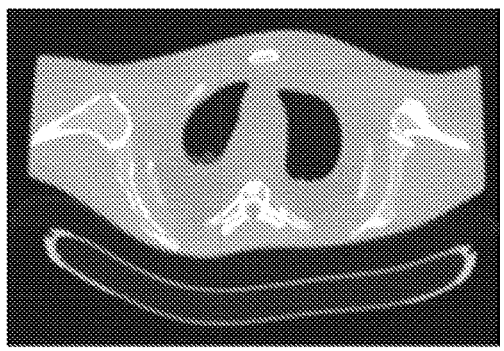
FIGS. 10(a)-(f) show influence of registration accuracy on the PWLS-PINL method of the present invention in low-dose image reconstruction from sinogram data acquired at 17 mAs, 120 kVp.
Figure 10B:
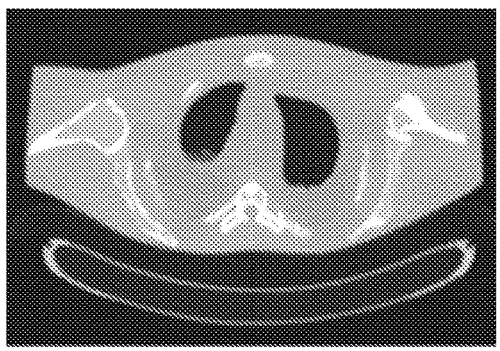
Figure 10C:
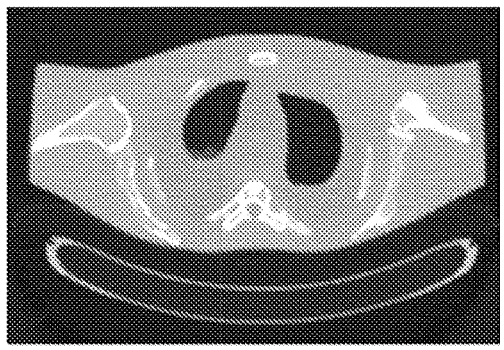
Figure 10D:
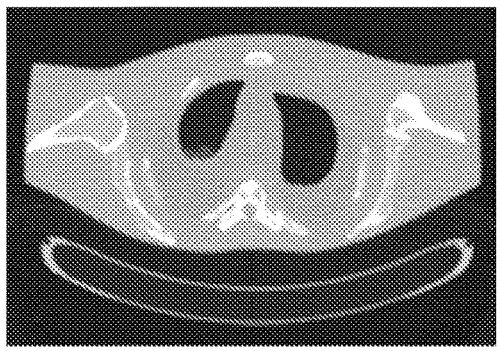
Figure 10E:
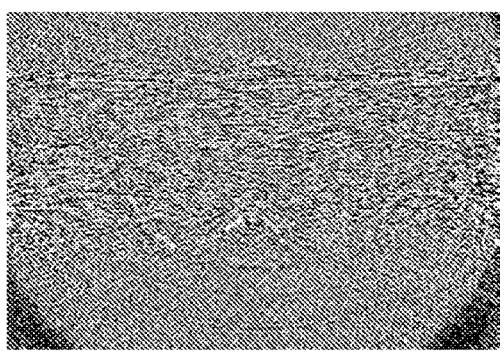
Figure 10F:
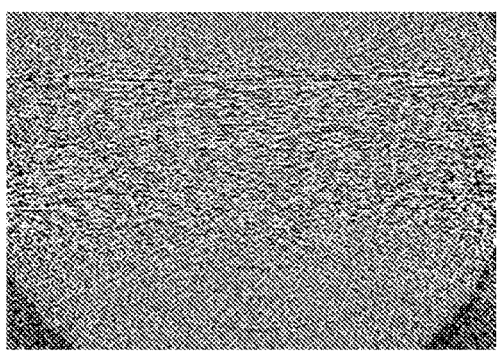

FIGS. 10(a)-(f) are images showing the influence of the registration accuracy on the PWLS-PINL method in the low-dose image reconstruction from the sinogram data acquired at 17 mAs, 120 kVp; with FIG. 10(a) showing an elastic deformed FBP image from an original reconstructed from sinogram data acquired at 100 mAs, 120 kVp; FIG. 10(b) showing the corresponding registered image by using the B-spline based registration algorithm; FIG. 10(c) showing the image reconstructed by the PWLS-PINL method from the sinogram data acquired at 17 mAs, 120 kVp using FIG. 10(a) as the prior-image; (d) the image reconstructed by the PWLS-PINL method using FIG. 10(b) as the prior-image from the sinogram data acquired at 17 mAs, 120 kVp; FIG. 10(e) showing the difference image between FIG. 10(c) and FIG. 2(a); and FIG. 10(f) showing the difference image between FIG. 10(d) and FIG. 2(a), with all images displayed in a same window.

In particular, FIGS. 10(a) and (b) show the elastic deformed FBP image and the corresponding registered FBP image, respectively, with deformation between the two images being significant. FIG. 10(c) shows the image reconstructed by the PWLS-PINL method using FIG. 10(a) as the prior-image. FIG. 10(d) shows the image reconstructed by the PWLS-PINL method using FIG. 10(b) as the prior-image. For both reconstructions of FIGS. 10(c) and 10(d), h was $2.0 \times 10^{-3}$ and β was $2.0 \times 10^4$. FIG. 10(e) shows a corresponding difference image between FIG. 10(c) and FIG. 2(a). FIG. 10(f) shows a corresponding difference image between FIG. 10(d) and FIG. 2(a). These difference images indicate that the performance of the PWLS-PINL method is not sensitive to the deformed prior image when a large search-window N is used to minimize the influence of the mis-registration. In other words, the present PWLS-PINL method does not heavily depend on the prior image registration accuracy. In practice, a rough registration may be sufficient.

For a numerical XCAT phantom study, adjacent slices of the normal-dose images were used as the prior image to induce the desired-image reconstruction by the PICCS and PWLS-PINL methods from the low-dose sinogram data. FIGS. 11(a)-(d) and 12(a)-(d) show a resultant influence of mismatch between two different prior images and desired images on the PWLS-PINL and PICCS methods, respectively.

Figure 11A:
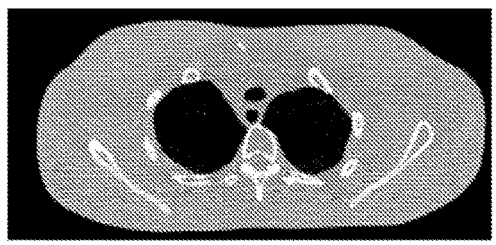
FIGS. 11(a)-(d) show mismatch influence between a first prior image and a desired image based on performance of PWLS-PINL and PICCS methods.
Figure 11B:
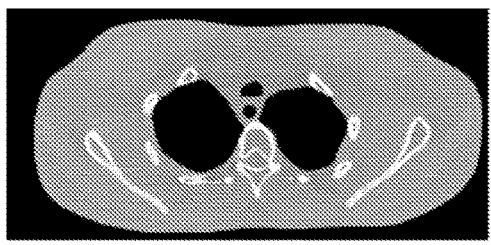
Figure 11C:
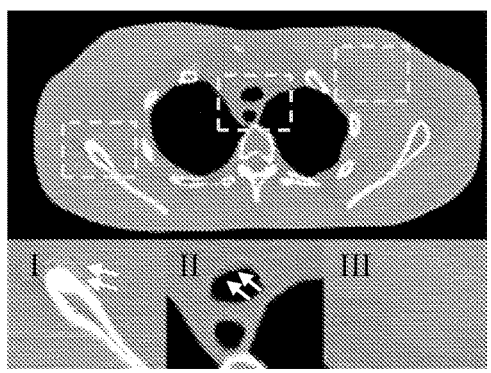
Figure 11D:
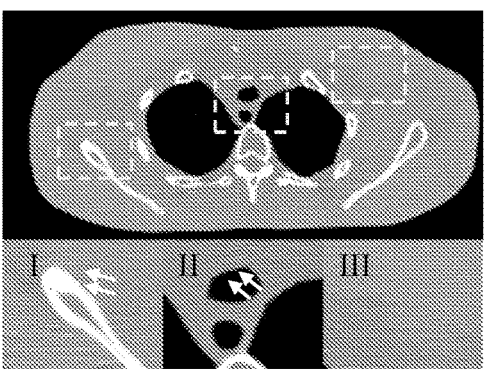

FIGS. 11(a)-(d) show influence of the mismatch between first prior image and desired image on performance of the PWLS-PINL and PICCS methods; with FIG. 11(a) showing the FBP image reconstructed with ramp filter from the low-dose sinogram data; FIG. 11(b) showing the unregistered prior image reconstructed from the normal dose sinogram data using the FBP method with ramp filter; FIG. 11(c) showing the image reconstructed by the PICCS method from the low-dose sinogram data using FIG. 11(b) as the prior-image ($\alpha=0.7$, $\lambda=8.0 \times 10^{-3}$); and FIG. 11(d) showing the image reconstructed by the PWLS-PINL method from the low-dose sinogram data by using FIG. 11(b) as the prior-image (N=35×35, n=5×5, $h=1.0 \times 10^{-3}$, $Q=5.0 \times 10^5$). The zoomed ROIs indicated by three squares in FIG. 11(c) and FIG. 11(d) are displayed at the bottom, respectively, with all images displayed in a same window.

Figure 12A:
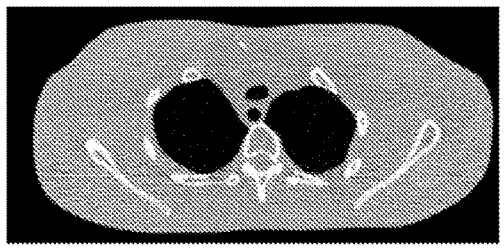
FIGS. 12(a)-(d) show mismatch influence between a second prior image and the desired image based on performance of PWLS-PINL and PICCS methods.
Figure 12B:
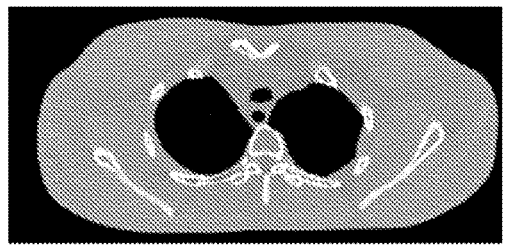
Figure 12C:
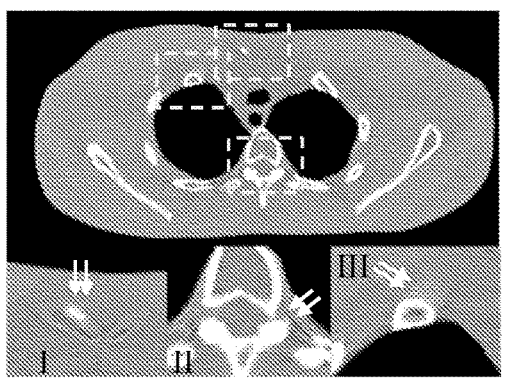
Figure 12D:
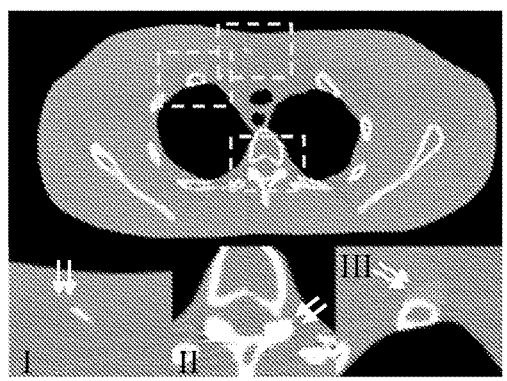

FIGS. 12(a)-(d) show influence of the mismatch between second prior image and desired image on performance of the PWLS-PINL and PICCS methods; with FIG. 12(a) showing the FBP image reconstructed with ramp filter from the low-dose sinogram data; FIG. 12(b) showing the unregistered prior-image reconstructed from the normal dose sinogram data using the FBP method with ramp filter; FIG. 12(c) showing the image reconstructed by the PICCS method from the low-dose sinogram data using FIG. 12(b) as the prior-image ($\alpha=0.7$, $\lambda=8.0 \times 10^{-3}$); and FIG. 12(d) showing the image reconstructed by the PWLS-PINL method from the low-dose sinogram data by using FIG. 12(b) as the prior-image (N=35×35, n=5×5, $h=1.0 \times 10^3$, $\beta=5.0 \times 10^5$). The zoomed ROIs indicated by three squares in FIG. 12(c) and FIG. 12(d) are displayed at the bottom, respectively, with all images displayed in a same window.

In particular, FIGS. 11(a) and 12(a) show the FBP images reconstructed with ramp filter from the low-dose sonogram data; and FIGS. 11(b) and 12(b) show the unregistered prior images reconstructed from the normal-dose sinogram data by the FBP method with ramp filter. The bone structure at the top of FIG. 11(a) does not appear in FIG. 11(b), but appears large in FIG. 12(b) due to the different slice selections. These features types were used to analyze the influence of prior information on the desired-image reconstruction. FIGS. 11(c) and 12(c) show the images reconstructed by the PICCS method from the low-dose sinogram data using FIGS. 11(b) and 12(b) as the prior-image, respectively. The zoomed ROIs at the bottom of each sub-figure show the pseudo boundaries from the PICCS method. The results suggest that some local mismatches between the prior and current images may propagate into the desired-image. However, FIGS. 11(d) and 12(d) show that the PWLS-PINL method with the same prior-image can deal with the mismatches between the prior and current images. These results indicate that the performance of the PWLS-PINL method is not sensitive to the mismatched prior images when a relatively large search-window is used to minimize the influence of the mismatch regions. In other words, the present PWLS-PINL method does not heavily depend on the prior-image mismatch accuracy, and a rough registration may be sufficient in practice.

For low-contrast detection ability, as shown in FIG. 11(c), box III and FIG. 11(d), box III, the PICCS method appears to perform better than the PWLS-PINL method in the matched regions. However, as shown in the zoomed ROI of FIGS. 11(c) and 12(c), the PWLS-PINL method outperforms the PICCS method when the low contrast features in the desired-image are different from those in the prior image.

FIGS. 13(a)-13(f) show chest CT images reconstructed by five different methods from two different sinogram data obtained from a patient study. FIGS. 13(a)-13(f) show clinical chest CT image reconstructions obtained from patient study; with FIG. 13(a) showing the image reconstructed by the FBP method with ramp filter from the sinogram data acquired at 200 mAs, 120 kVp, which is used as the prior image for the PWLS-PINL and PICCS methods; FIG. 13(b) showing an image reconstructed by the FBP with ramp filter from the sinogram data acquired at 20 mAs, 120 kVp; FIG. 13(c) showing image reconstructed by the PWLS-NL method from the sinogram data acquired at 20 mAs, 120 kVp (N=21×21, n=5×5, $h=0.6 \times 10^{-3}$, $\beta=1.0 \times 10^4$); FIG. 13(d) showing image reconstructed by the PICCS method from the sinogram data acquired at 20 mAs, 120 kVp ($\alpha=0.5$, $\lambda=0.1$); FIG. 13(e) showing the image reconstructed by the GDSIR method from the sinogram data acquired at 20 mAs, 120 kVp ($\gamma=4 \times 10^{-2}$); and FIG. 13(f) showing image reconstructed by the PWLS-PINL method from the sinogram data acquired at 20 mAs, 120 kVp (N=41×41, n=5×5, $h=0.6 \times 10^{-3}$, $\beta=1.0 \times 10^4$), with all images displayed in the window [0 0.02] mm$^{-1}$.

In particular, FIG. 13(a) shows the image reconstructed by the FBP method with ramp filter from the sinogram data acquired at 200 mAs, 120 kVp, which was used as the prior image for the PWLS-PINL, PICCS and GDSIR methods. FIG. 13(b) shows the image reconstructed by the FBP with ramp filter from the sinogram data acquired at 20 mAs, 120 kVp. The anatomical structures between two FBP images are mostly similar except some noticeable organ elastic deformation as indicated by the rectangles in FIGS. 13(a) and 13(b) because of heteronomous breathing or heartbeat, with noise-induced streak artifacts observable in FIG. 13(b). FIG. 13(c) shows the image reconstructed by the PWLS-NL method from the sinogram data acquired at 20 mAs, 120 kVp. FIG. 13(d) shows the image reconstructed by the PICCS method using FIG. 13(a) as the prior image. Most of the noise is mitigated by the TV term of the PICCS objective function, whereas some deceptive structures appear in the mismatched areas. This phenomenon indicates that the edge structure in the prior images may have been passed to the current images. FIG. 13(e) shows the image reconstructed by the GDSIR method from the sinogram data acquired at 20 mAs, 120 kVp. The global dictionary was learned from patches extracted from FIG. 13(a). It can be seen most of the noise is removed without introducing new fake structure, but noticeable streak artifacts still exist. FIG. 13(f) shows the image reconstructed by the PWLS-PINL method from the sinogram data acquired at 20 mAs, 120 kVp.

Figure 14A:
FIGS. 14(a)-14(d) are zoomed ROIs of the clinical chest CT image reconstructions of FIG. 13.
Figure 14B:
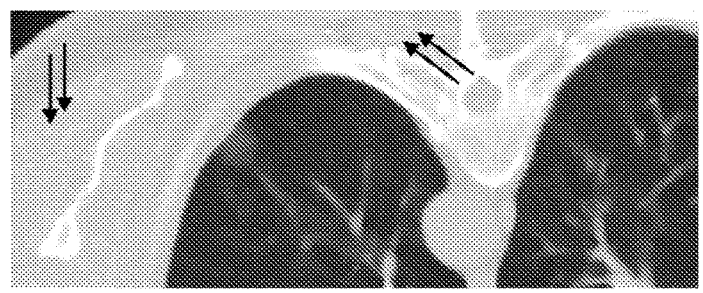
Figure 14C:
Figure 14D:
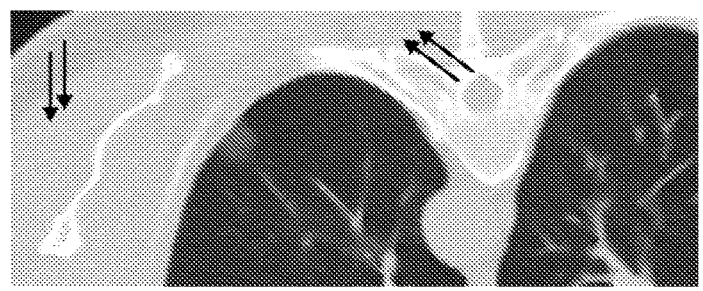

To illustrate further the performance of the PWLS-based methods, the zoomed ROIs are shown in FIGS. 14(a)-(d), which provide zoomed ROIs of the clinical chest CT image reconstructions of FIG. 13, with FIG. 14(a) providing an image reconstructed by the PWLS-NL method from the sinogram data acquired at 20 mAs, 120 kVp (N=21×21, n=5×5, h=0.6×10$^{-3}$, β=1.0×10$^4$); FIG. 14(b) providing an image reconstructed by the PICCS method from the sinogram data acquired at 20 mAs, 120 kVp (α=0.5, λ=0.1); FIG. 14(c) providing the image reconstructed by the GDSIR method from the sinogram data acquired at 20 mAs, 120 kVp (γ=4×10$^{-2}$); and FIG. 14(d) providing an image reconstructed by the PWLS-PINL method from the sinogram data acquired at 20 mAs, 120 kVp (N=41×41, n=5×5, h=0.6× 10$^{-3}$, β=1.0×10$^4$), with all images displayed in the window [0 0.02] mm-1.

The results show that the present PWLS-PINL method can achieve significant gains over the other methods in terms of reconstruction accuracy by visual inspection. In the implementation of the four PWLS-based methods, the FBP image reconstructed with ramp filter, i.e., FIG. 13(b), was used as the initial image. All the parameters were selected by visual inspection for eye-appealing results, together with the normal-dose FBP image (i.e., FIG. 13(a)) for comparison.

In medical clinics, several situations exist where repeated tomographic acquisitions are prescribed. In these cases, substantial similarity exists among images in the acquisition sequence. As a result, a previously scanned normal-dose CT image may provide strong prior information for subsequent iterative image reconstruction from the projection data with a low-dose protocol. For example, Chen et al. proposed the PICCS method for CT iterative image reconstruction from the spare-view measurements using a high-quality reference image. Ma et al. proposed the ndiNLM filter for low-dose CT image restoration using the previously scanned CT image without requiring the accurate image registration processing due to its patch-based search mechanism. The present invention provides a prior-image induced NL regularization term for PWLS image reconstruction, i.e., the PWLS-PINL, with results using both phantom and patient data indicating that that the algorithm robustly incorporates redundant information from previously acquired images without requiring accurate image registration. Moreover, a substantial improvement in image quality was observed compared with the traditional methods if the prior images were not incorporated.

To realize radiation dose reduction by reducing the x-ray tube current and exposure time (mAs) in repeated CT scans, an iterative image reconstruction algorithm via the penalized weighted least-squares (PWLS) criteria is developed by incorporating a Prior-image Induced NL (PINL) regularization, to yield a clinically acceptable X-ray CT image with lower mAs. For simplicity, the PWLS-PINL algorithm is provided in Equation (2), above, where y represents the obtained sinogram data, μ is the vector of attenuation coefficients to be estimated, Σ is a diagonal matrix with the ith element of $\sigma_i^2$ which is the variance of sinogram data y, operator H represents the system or projection matrix, and $R_{PINL}(\mu)$ represents the PINL regularization term, which is defined by Equation (5), above, where $N_j$ denotes the search-window, $\mu_{prior,k}^{reg}$ denotes the image intensity at the voxel k in the registered prior image domain, weight w(k, j) quantifies the similarity between the voxel j in the object image μ and the voxel k in the registered prior image $\mu_{prior}^{reg}$, respectively, which can be expressed by Equations (6)-(8), above, where $n_j$ and $n_k$ denote two local similarity neighborhoods, i.e., patch-windows, centered at the voxels j and k, respectively; $\mu(n_j)$ and $\mu_{prior}^{reg}(n_k)$ denote the vector of neighborhood voxel values restricted in the patch-windows $n_j$ and $n_k$, respectively; notation $\|\cdot\|_2^2$ represents a 2D Euclidean distance between two patch-windows; and h is a parameter controlling the decay of the exponential function.

To solve the optimization problem, a binary optimal scheme automatically adjusts the weight w(k, j) according to similarity between the patch-windows in the current estimation $\mu^m$ (m is the iterative index) and the registered prior image $\mu_{prior}^{reg}$ during each iteration. The PWLS-PINL method for X-ray CT image reconstruction has three main steps, as follows.

First, an NL weight calculation is performed. For a first iteration, $\mu^m=\mu^0$, with $\mu^0$ being set as a uniform value or reconstructed by a Filtered Back-Projection (FBP). Given the current image estimation $\mu^m$ and the registered prior image $\mu_{prior}^{reg}$, the NL weights w can be calculated.

Second, Successive Over-Relaxation (SOR) optimization is performed, with an iterative SOR algorithm utilized to yield a new image estimation with voxel-wise calculation, i.e., $\mu_j^{m+1}$, which can be expressed as Equation (22):

$$\tilde{\mu}_j^{m+1} = \frac{H_j^T \Sigma^{-1} r^m + S_j \mu_j^m + \beta \sum_{k \in N_j} w(k, j)\mu_{prior,k}^{reg}}{S_j + \beta \sum_{k \in N_j} w(k, j)}, \quad (22)$$

$$\mu_j^{m+1} = \max\{0, (1-\omega)\mu_j^m + \omega\tilde{\mu}_j^{m+1}\}$$

where $r^m = y - H\mu^m$ represents the residual between the obtained sinogram data and the estimated one in the m-th iteration, $S_j$ is calculated as $S_j = H_j^T \Sigma^{-1} H_j$, and parameter ω is the relax factor, which satisfies 0≤ω≤1.

Third, a cycle update is performed, with update $\mu^{m+1}$ using the aforementioned steps in each iteration cycle, based on stop criterion evaluation, as described below.

Figure 15:
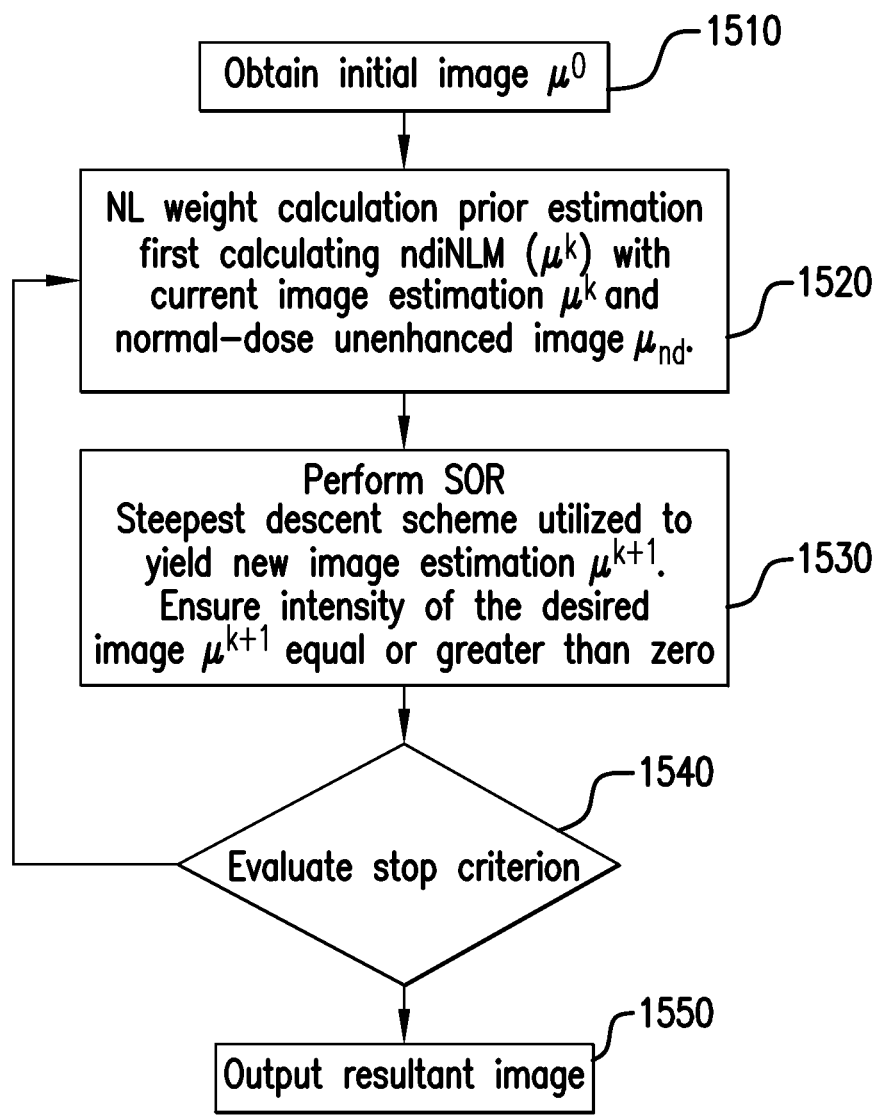
FIG. 15 is a flowchart summarizing the PWLS-PINL algorithm, according to the present invention and FIG. 16 provides an anthropomorphic torso phantom reconstruction showing squares of CNR measurement of images.

FIG. 15 is a flowchart summarizing the PWLS-PINL algorithm. In step 1510, an initial image $\mu^0$ is obtained, and an NL weight calculation is performed in step 1520. In the NL weight calculation, given the current image estimation $\mu^m$ and the registered prior image $\mu_{prior}^{reg}$, the NL weights are first calculated with $\mu^m$ and $\mu_{prior}^{reg}$. In step 1530, SOR optimization is performed, with an iterative SOR algorithm utilized to yield new image estimation, i.e., $\mu^{m+1}$, and the intensity of the new image estimation $\mu^{m+1}$ is ensured to be equal or greater than zero.

In step 1540, a stop criterion is evaluated. For the stop criterion, a determination is made of whether a difference between two successive iterations is less than a predefined threshold, which can be set as a one percent change between two successive iterations. If the evaluation in step 1540 indicates that the stop criterion is satisfied, a resultant image is output to a display in step 1550. If the evaluation in step 1540 indicates that the stop criterion is not satisfied, the NL weight calculation of step 1520 is repeated, followed by steps 1530 and 1540, as described above.

The present algorithm can be applied to sequences of acquired tomographic data, such as lung nodule surveillance, image-guided biopsy needle and volumetric CBCT imaging during a radiation therapy. Because the prior image may be offset or rotated with respect to anatomy at the time of imaging, a coarse registration is applied in the implementation of the present PWLS-PINL method, to reduce the computational burden based on a selected median size search window.

Two conventional image based methods, i.e., the PICCS and GDSIR, were compared to the method of the present invention. The PICCS and PWLS-PINL methods can be regarded as a voxel updating technique while the GDSIR method is a patch updating technique. As discussed above, the PICCS method cannot achieve satisfactory performance in suppressing noise-induced artifacts as the misalignments between the prior-images, and desired-images are significant. In addition, the GDSIR method also cannot effectively deal with the noise-induced artifacts in ultra-low-dose scans. Meanwhile, the present PWLS-PINL method can relax the tradeoff of introduction of fake structures and reduces noise-induced streak artifacts utilizing non-local means processing in image restoration. In addition, the NL mean algorithm, as a post-processing technique for low-dose CT image restoration, also works well in some cases. However, when the projection data was seriously corrupted by excessive x-ray photon noise, the associative FBP image will suffer from serious noise-induced streak artifacts and the NL means algorithm then cannot yield satisfactory results due to an inability to effectively suppress streak artifacts. Meanwhile, the present PWLS-PINL method, by modeling several important physical and statistical factors including detector geometry, photon statistics and electronic background noise, can yield more accurate results than the NL means algorithm from the noisy projection measurements.

For implementation of the PWLS-PINL method, four parameters, i.e., search-window N, patch-window n, control parameter h, and hyper-parameter $\beta$, were selected by visual inspection based on operator eye-appeal, together with a normal-dose image for comparison. In practice, to reduce computing burden, the size of the search-window is limited to an appropriate use, with the search-window large enough to obtain more similar information while minimizing the influence of the mismatched tissues. Hence, search-window N is optimally determined by fully considering both registration accuracy and degree of overall structure changes between the to-be-reconstructed and prior images. For selection of the patch-window, extensive experiments showed that a 5×5 patch-window as being adequate for effective noise and artifacts suppression while retaining computational efficiency. As for selection of h and $\beta$, the sizes of the search- and patch-windows were briefly fixed and methods for adaptive optimization were not considered, but results obtained manually using a broad range of parameter values, with the results visual inspection and quantitative measurements, as a trial and error process. Theoretical studies in optimizing the non-local relevant parameters have already been conducted using a SURE approach, which provided a useful technique to determine the parameters in the present algorithm. See, D. V. De Ville, et al., *SURE-based Non-local Means*, IEEE Signal Processing Letters, Vol. 16, no. 11, pp. 973-976, November 2009; and V. Duval, et al., *On the Parameter Choice for the Non-Local Means*," Tech. Rep. hal-00468856, HAL, 2010.

For the modified iterative successive over-relaxation algorithm, as a version of the widely-used One-Step-Late (OSL) iteration scheme, the present PWLS-PINL can be feasibly and effectively implemented using the present algorithm joint optimal reconstruction strategy, as described above. However, due to the fact that weight w(k, j) in Equation (6) depends on unknown image intensity, the present PINL regularization in Equation (5) is nonconvex for a global optimization.

To address a potential drawback of the PWLS-PINL algorithm to update the NL weights matrix increasing the computational burden, parameters (NL weights matrix) interleaved with more frequent OSL steps are updated at a reduced frequency; and/or fast computers and dedicated hardware are utilized to provide parallel iterative image reconstruction.

In a preferred aspect, a system for using an algorithm of the above method includes a processor configured to execute the above described method. Specifically, the methods of the present invention are implemented in systems that use software run on a computer processor to carry out the above described methods. While in preferred embodiments, the methods are carried out in an automated format, entirely within the computer processor, it should be understood that one or more components may be carried out by a human and that the methods may involve human interaction or intervention at one or more points.

The computer processor for conducting aspects of the methods of the present invention may be housed in devices that include desktop computers, scientific instruments, hand-held devices, personal digital assistants, phones, a non-transitory computer readable medium, and the like. The methods need not be carried out on a single processor. For example, one or more steps may be conducted on a first processor, while other steps are conducted on a second processor. The processors may be located in the same physical space or may be located distantly. In some such embodiments, multiple processors are linked over an electronic communications network, such as the Internet. Preferred embodiments include processors associated with a display device for showing the results of the methods to a user or users, outputting results as a video image. The processors may be directly or indirectly associated with information databases, which include hospital databases.

As used herein, the terms processor, central processing unit, and CPU are used interchangeably and refer to a device that is able to read a program from a computer memory, e.g., ROM or other computer memory, and perform a set of steps according to the program. The terms computer memory and computer memory device refer to any storage media readable by a computer processor. Examples of computer memory include, but are not limited to, RAM, ROM, computer chips, digital video discs, compact discs, hard disk drives and magnetic tape. Also, computer readable medium refers to any device or system for storing and providing information, e.g., data and instructions, to a computer processor, DVDs, CDs, hard disk drives, magnetic tape and servers for streaming media over networks. As used herein, encode refers to the process of converting one type of information or signal into a different type of information or signal to, for example, facilitate the transmission and/or interpretability of the information or signal. For example, image files can be converted into, i.e., encoded into, electrical or digital information.

While the invention has been shown and described with reference to certain exemplary embodiments of the present invention thereof, it will be understood by those skilled in the art that various changes in from and details may be made therein without departing from the spirit and scope of the present invention as defined by the appended claims and equivalent thereof.

What is claimed is:

1. A method for operating an X-ray Computed Tomography (CT) scanning device, the method comprising:
   acquiring, by the CT scanning device, a plurality of images of an object;
   obtaining an initial image from the plurality of images;
   performing a calculation of NonLocal (NL) weight utilizing a current image estimation and a registered prior image;

performing a Successive Over-Relaxation (SOR) optimization to yield a new image estimation, with an intensity of the new image estimation being equal or greater than zero;

performing a cycle update that repeats the obtaining of the initial image, the performing of the NL weight calculation, and the SOR optimization;

generating an image of the object utilizing the new image estimation obtained from the SOR optimization; and outputting a resultant image when a stop criterion is met.

2. The method of claim 1, further comprising performing a prior-image induced NL regularization utilizing a potential function of:

$$R_{PINL}(\mu) = \sum_j \sum_{k \in N_j} w(k, j)(\mu_j - \mu_{prior,k}^{reg})^2,$$

where $\mu_{prior}^{reg}$ denotes the registered prior image between a prior image $\mu_{prior}$ and a current image, and $N_j$ denotes a search-window.

3. The method of claim 1, wherein the SOR optimization yields a new image estimation according to:

$$\tilde{\mu}_j^{m+1} = \frac{H_j^T \Sigma^{-1} r^m + S_j \mu_j^m + \beta \sum_{k \in N_j} w(k, j) \mu_{prior,k}^{reg}}{S_j + \beta \sum_{k \in N_j} w(k, j)},$$

$$\mu_j^{m+1} = \max\{0, (1 - \omega)\mu_j^m + \omega \tilde{\mu}_j^{m+1}\}$$

with $r^m = y - H\mu^m$ being a residual between obtained sinogram data and an estimated one in an m-th iteration, $S_j = H_j^T \Sigma^{-1} H_j$, and a relax factor $\omega$ satisfies $0 \leq \omega \leq 1$.

4. The method of claim 1, wherein the output resultant image is utilized for one of lung nodule surveillance, image-guided biopsy needle, and volumetric Cone Beam CT imaging performed during a radiation therapy course.

* * * * *

UNITED STATES PATENT AND TRADEMARK OFFICE
CERTIFICATE OF CORRECTION

| | | |
|---|---|---|
| PATENT NO. | : 9,558,570 B2 | Page 1 of 1 |
| APPLICATION NO. | : 14/784714 | |
| DATED | : January 31, 2017 | |
| INVENTOR(S) | : Jerome Z. Liang et al. | |

It is certified that error appears in the above-identified patent and that said Letters Patent is hereby corrected as shown below:

In Column 1, please add the following after the Priority paragraph:

GOVERNMENT SUPPORT
This invention was made with government support under grant number CA143111 awarded by the National Institutes of Health. The government has certain rights in the invention.

Signed and Sealed this
Thirteenth Day of June, 2017

Joseph Matal
*Performing the Functions and Duties of the*
*Under Secretary of Commerce for Intellectual Property and*
*Director of the United States Patent and Trademark Office*